United States Patent
Hochman et al.

(10) Patent No.: US 11,471,595 B2
(45) Date of Patent: Oct. 18, 2022

(54) METHOD AND APPARATUS FOR PERFORMING A PERIPHERAL NERVE BLOCK

(71) Applicant: Milestone Scientific, Inc., Livingston, NJ (US)

(72) Inventors: Mark N. Hochman, Great Neck, NY (US); Olivier Choquet, Castenau le lez (FR)

(73) Assignee: MILESTONE SCIENTIFIC, INC., Livingston, NJ (US)

( * ) Notice: Subject to any disclaimer, the term of this patent is extended or adjusted under 35 U.S.C. 154(b) by 359 days.

(21) Appl. No.: 16/605,580

(22) PCT Filed: May 4, 2018

(86) PCT No.: PCT/US2018/031096
§ 371 (c)(1),
(2) Date: Oct. 16, 2019

(87) PCT Pub. No.: WO2018/204789
PCT Pub. Date: Nov. 8, 2018

(65) Prior Publication Data
US 2021/0290843 A1   Sep. 23, 2021

Related U.S. Application Data

(63) Continuation-in-part of application No. 15/587,119, filed on May 4, 2017, now abandoned.
(Continued)

(51) Int. Cl.
*A61M 5/168* (2006.01)
*A61M 5/158* (2006.01)
(Continued)

(52) U.S. Cl.
CPC ....... *A61M 5/16854* (2013.01); *A61B 5/1106* (2013.01); *A61M 5/158* (2013.01);
(Continued)

(58) Field of Classification Search
CPC .............. A61M 5/16854; A61M 5/158; A61M 5/16877; A61M 2205/3344;
(Continued)

(56) References Cited

U.S. PATENT DOCUMENTS

| | | |
|---|---|---|
| 3,867,934 A | 2/1975 | Louisa |
| 4,356,826 A | 11/1982 | Kubota |

(Continued)

FOREIGN PATENT DOCUMENTS

| | | |
|---|---|---|
| DE | 202005019430 | 2/2006 |
| EP | 0303824 | 2/1989 |

(Continued)

OTHER PUBLICATIONS

International Search Report & Written Opinion issued in International Application No. PCT/US20/29857 dated Jul. 21, 2020.
(Continued)

*Primary Examiner* — James D Ponton
(74) *Attorney, Agent, or Firm* — Niels Haun; Dann, Dorfman, Herrell & Skillman, P.C.

(57) ABSTRACT

A system for infusing medication into a mammalian subject is provided. The system includes an injection system for controlling a flow of fluid from a fluid reservoir to a needle. A sensor is provided that detects a characteristic indicative of the fluid pressure in the needle. The injection system controls the flow of fluid to the needle in response to the characteristic detected by the sensor and the sensor continuously detects the characteristic as the needle is inserted into the subject. The system further includes a conductive element for providing electric nerve stimulation, wherein the
(Continued)

system provides electric nerve stimulation in response to the sensor detecting a pressure exceeding an upper limit.

13 Claims, 7 Drawing Sheets

Related U.S. Application Data

(60) Provisional application No. 62/501,546, filed on May 4, 2017.

(51) Int. Cl.
*A61B 5/11* (2006.01)
*A61N 1/05* (2006.01)
*A61N 1/36* (2006.01)

(52) U.S. Cl.
CPC ....... *A61M 5/16877* (2013.01); *A61N 1/0502* (2013.01); *A61N 1/0551* (2013.01); *A61N 1/36031* (2017.08); *A61N 1/36034* (2017.08); *A61M 2205/3344* (2013.01); *A61M 2230/08* (2013.01)

(58) Field of Classification Search
CPC ............ A61N 1/36031; A61N 1/36034; A61N 1/0502; A61N 1/0551; A61B 5/1106
See application file for complete search history.

(56) References Cited

U.S. PATENT DOCUMENTS

| | | |
|---|---|---|
| 4,403,988 A | 9/1983 | Binard |
| 4,518,383 A | 5/1985 | Evans |
| 4,624,659 A | 11/1986 | Goldberg |
| 4,679,567 A | 7/1987 | Hanlon |
| 4,790,821 A | 12/1988 | Stines |
| 4,801,293 A | 1/1989 | Jackson |
| 4,893,630 A | 1/1990 | Bray, Jr. |
| 4,988,337 A | 1/1991 | Ito |
| 4,998,914 A | 3/1991 | Wiest |
| 5,100,390 A | 3/1992 | Lubeck |
| 5,178,603 A | 1/1993 | Prince |
| 5,197,895 A | 3/1993 | Stupecky |
| 5,267,565 A | 12/1993 | Beard |
| 5,269,762 A | 12/1993 | Armbruster |
| 5,295,967 A | 3/1994 | Rondelet |
| D348,101 S | 6/1994 | Poli |
| 5,378,231 A | 1/1995 | Johnson |
| 5,405,269 A | 4/1995 | Stupecky |
| D360,259 S | 7/1995 | Ijiri |
| 5,520,650 A | 5/1996 | Zadini |
| 5,611,778 A | 3/1997 | Brinon |
| 5,660,567 A | 8/1997 | Nierlich |
| 5,681,285 A | 10/1997 | Ford |
| 5,690,618 A | 11/1997 | Smith |
| D390,654 S | 2/1998 | Alsberg |
| 5,727,553 A | 3/1998 | Saad |
| 5,810,770 A | 9/1998 | Chin |
| D409,148 S | 5/1999 | Yuji |
| 5,902,273 A | 5/1999 | Yang |
| 5,954,701 A | 9/1999 | Matalon |
| 6,022,337 A | 2/2000 | Herbst |
| 6,024,576 A | 2/2000 | Bevirt |
| 6,120,457 A | 9/2000 | Coombes |
| 6,126,610 A | 10/2000 | Rich |
| 6,159,161 A | 12/2000 | Hodosh |
| D436,927 S | 1/2001 | Hogan |
| 6,200,289 B1 | 3/2001 | Hochman |
| 6,456,874 B1 * | 9/2002 | Hafer ................ A61B 17/3401 604/21 |
| 6,468,241 B1 | 10/2002 | Gelfand |
| 6,569,147 B1 | 5/2003 | Evans |
| 6,652,482 B2 | 11/2003 | Hochman |
| 6,695,806 B2 | 2/2004 | Gelfand |
| 6,705,990 B1 | 3/2004 | Gallant |
| 6,716,192 B1 | 4/2004 | Orosz, Jr. |
| 6,773,417 B2 | 8/2004 | Fitzgibbons |
| 6,786,885 B2 | 9/2004 | Hochman |
| 6,866,648 B2 | 3/2005 | Hadzic |
| 6,886,648 B1 | 5/2005 | Hata |
| 6,887,216 B2 | 5/2005 | Hochman |
| 6,942,637 B2 | 9/2005 | Cartledge |
| 7,022,072 B2 | 4/2006 | Fox |
| 7,198,602 B2 | 4/2007 | Eide |
| 7,285,100 B2 | 10/2007 | Lemaire |
| D556,910 S | 12/2007 | Reihanifam |
| 7,335,162 B2 | 2/2008 | Eide |
| 7,364,570 B2 | 4/2008 | Gerondale |
| 7,395,214 B2 | 7/2008 | Shillingburg |
| 7,449,008 B2 | 11/2008 | Hochman |
| D600,644 S | 9/2009 | Leung |
| 7,604,602 B2 | 10/2009 | Roteliuk |
| 7,618,409 B2 | 11/2009 | Hochman |
| 7,635,338 B2 | 12/2009 | Eide |
| 7,641,637 B2 | 1/2010 | Gerondale |
| 7,727,224 B2 | 6/2010 | Hadzic |
| 7,775,985 B2 | 8/2010 | Eide |
| D630,727 S | 1/2011 | Martin |
| 7,896,833 B2 | 3/2011 | Hochman |
| 7,922,689 B2 | 4/2011 | Lechner |
| D642,984 S | 8/2011 | Junichi |
| 8,002,736 B2 | 8/2011 | Patrick |
| 8,016,763 B2 | 9/2011 | Eide |
| 8,079,976 B2 | 12/2011 | Patrick |
| 8,137,312 B2 | 3/2012 | Sundar |
| 8,142,414 B2 | 3/2012 | Patrick |
| 8,197,443 B2 | 6/2012 | Sundar |
| 8,256,984 B2 | 9/2012 | Fathallah |
| 8,262,584 B2 | 9/2012 | Eide |
| D669,096 S | 10/2012 | Katsura |
| D669,165 S | 10/2012 | Estes |
| 8,282,565 B2 | 10/2012 | Mahapatra |
| 8,308,654 B2 | 11/2012 | Eide |
| 8,398,564 B2 | 3/2013 | Eide |
| D679,379 S | 4/2013 | Katsura |
| 8,444,592 B2 | 5/2013 | Williams |
| 8,480,630 B2 | 7/2013 | Mudd |
| D687,536 S | 8/2013 | Shafer |
| 8,545,440 B2 | 10/2013 | Patrick |
| 8,562,600 B2 | 10/2013 | Kirkpatrick |
| 8,684,947 B2 | 4/2014 | Eide |
| 8,764,668 B2 | 7/2014 | Roteliuk |
| 8,814,807 B2 | 8/2014 | Hulvershorn |
| 8,896,324 B2 | 11/2014 | Kroh |
| 8,926,525 B2 | 1/2015 | Hulvershorn |
| 8,992,481 B2 | 3/2015 | Mudd |
| 8,998,841 B2 | 4/2015 | Shen |
| D730,514 S | 5/2015 | Omer |
| 9,044,542 B2 | 6/2015 | Patrick |
| D734,475 S | 7/2015 | Ross |
| 9,084,550 B1 * | 7/2015 | Bartol ................ A61B 5/1106 |
| D736,370 S | 8/2015 | Bodwell |
| D741,811 S | 10/2015 | Solomon |
| 9,199,044 B2 | 12/2015 | Bangera |
| 9,205,204 B2 | 12/2015 | Bangera |
| 9,358,038 B2 | 6/2016 | Hulvershorn |
| 9,358,350 B2 | 6/2016 | Bangera |
| D760,888 S | 7/2016 | Friedrich |
| D765,832 S | 9/2016 | Solomon |
| 9,443,446 B2 | 9/2016 | Rios |
| 9,452,261 B2 | 9/2016 | Alon |
| 9,468,396 B2 | 10/2016 | Mahapatra |
| 9,504,790 B1 | 11/2016 | Hochman |
| 9,603,537 B2 | 3/2017 | Lechner |
| 9,642,534 B2 | 5/2017 | Mahapatra |
| 9,655,528 B2 | 5/2017 | Zhu |
| D801,519 S | 10/2017 | Sloss |
| D803,386 S | 11/2017 | Sloss |
| D803,387 S | 11/2017 | Kerwin |
| 9,888,881 B2 | 2/2018 | Hulvershorn |
| 9,901,679 B2 | 2/2018 | Shen |
| 9,956,341 B2 | 5/2018 | Hockman |
| 10,004,450 B2 | 6/2018 | Moskowitz |

(56) References Cited

U.S. PATENT DOCUMENTS

| | | |
|---|---|---|
| 10,117,673 B2 | 11/2018 | Luo |
| 10,220,180 B2 | 3/2019 | Hochman |
| 10,383,610 B2 | 8/2019 | Moskowitz |
| D859,634 S | 9/2019 | Hochman et al. |
| 10,406,285 B2 | 9/2019 | Anand |
| 10,463,838 B2 | 11/2019 | Hulvershorn |
| 10,602,958 B2 | 3/2020 | Silverstein |
| 2002/0016567 A1 | 2/2002 | Hochman |
| 2002/0016569 A1 | 2/2002 | Critchlow |
| 2002/0022807 A1 | 2/2002 | Duchon |
| 2002/0143294 A1 | 10/2002 | Duchon |
| 2003/0014006 A1 | 1/2003 | Alexandre |
| 2004/0035743 A1 | 2/2004 | Tighe |
| 2004/0149282 A1 | 8/2004 | Hickle |
| 2004/0215080 A1 | 10/2004 | Lechner |
| 2005/0004513 A1 | 1/2005 | Beyerlein |
| 2005/0004514 A1 | 1/2005 | Hochman |
| 2005/0096593 A1 | 5/2005 | Pope |
| 2005/0126304 A1* | 6/2005 | Sparks .............. G01F 1/8445 73/861.05 |
| 2006/0122555 A1 | 6/2006 | Hochman |
| 2006/0247657 A1 | 11/2006 | Trieu |
| 2007/0038143 A1 | 2/2007 | Christensen |
| 2007/0197922 A1 | 8/2007 | Bradley |
| 2008/0058702 A1 | 3/2008 | Arndt |
| 2008/0103408 A1 | 5/2008 | Denton |
| 2008/0281265 A1 | 11/2008 | Hochman |
| 2009/0131832 A1 | 5/2009 | Sacristan Rock |
| 2009/0149911 A1 | 6/2009 | Dacey, Jr. |
| 2009/0149912 A1 | 6/2009 | Dacey, Jr. |
| 2009/0171191 A1 | 7/2009 | Patrick |
| 2009/0210029 A1 | 8/2009 | Tsui |
| 2009/0221914 A1 | 9/2009 | Barrett |
| 2009/0326482 A1 | 12/2009 | Hochman |
| 2010/0022918 A1 | 1/2010 | Fujie |
| 2010/0030102 A1 | 2/2010 | Poston |
| 2010/0049270 A1 | 2/2010 | Pastore |
| 2010/0056932 A1 | 3/2010 | Roteliuk |
| 2010/0179488 A1 | 7/2010 | Spiegel |
| 2010/0274191 A1 | 10/2010 | Ting |
| 2011/0021905 A1 | 1/2011 | Patrick |
| 2011/0046477 A1 | 2/2011 | Hulvershorn |
| 2011/0054353 A1 | 3/2011 | Hulvershorn |
| 2011/0060229 A1 | 3/2011 | Hulvershorn |
| 2011/0087166 A1 | 4/2011 | Davis |
| 2011/0112511 A1 | 5/2011 | Singer |
| 2011/0120566 A1 | 5/2011 | Ohmi |
| 2011/0190596 A1 | 8/2011 | Hacker |
| 2011/0270179 A1 | 11/2011 | Ouyang |
| 2011/0288481 A1 | 11/2011 | Mudd |
| 2011/0298628 A1 | 12/2011 | Vad |
| 2011/0301500 A1 | 12/2011 | Maguire |
| 2012/0022407 A1 | 1/2012 | Lechner |
| 2012/0083760 A1 | 4/2012 | Ledford |
| 2012/0101410 A1 | 4/2012 | Lechner |
| 2012/0232389 A1 | 9/2012 | Guzman |
| 2012/0259237 A1 | 10/2012 | Axelrod |
| 2012/0289819 A1 | 11/2012 | Snow |
| 2012/0296176 A1 | 11/2012 | Herbst |
| 2013/0041258 A1* | 2/2013 | Patrick ................ A61M 5/142 600/439 |
| 2013/0053851 A1 | 2/2013 | Schmitz |
| 2013/0131633 A1 | 5/2013 | Mudd |
| 2013/0261533 A1 | 10/2013 | Norkunas |
| 2014/0012226 A1* | 1/2014 | Hochman ............. G16H 20/17 604/506 |
| 2014/0066891 A1 | 3/2014 | Burns |
| 2014/0121636 A1 | 5/2014 | Boyden |
| 2014/0121637 A1 | 5/2014 | Boyden |
| 2014/0207050 A1 | 7/2014 | Gonzalez |
| 2014/0221965 A1 | 8/2014 | Regittnig |
| 2014/0316268 A1 | 10/2014 | Kafiluddi |
| 2014/0343406 A1 | 11/2014 | Damjanovic |
| 2015/0150519 A1 | 6/2015 | Glenn |
| 2015/0283365 A1 | 10/2015 | Dacey, Jr. |
| 2015/0374929 A1 | 12/2015 | Hyde |
| 2016/0135712 A1 | 5/2016 | Holochwost |
| 2016/0136363 A1 | 5/2016 | McClellan |
| 2016/0228633 A1 | 8/2016 | Welsch |
| 2017/0106142 A1 | 4/2017 | Hochman |
| 2018/0064870 A1 | 3/2018 | Hochman |
| 2018/0087517 A1 | 3/2018 | Glenn |
| 2018/0116551 A1 | 5/2018 | Newman |
| 2018/0228968 A1 | 8/2018 | Hochman |

FOREIGN PATENT DOCUMENTS

| | | |
|---|---|---|
| EP | 0538259 | 4/1993 |
| FR | 2628625 | 9/1989 |
| HU | P8806113 | 10/1990 |
| HU | P0204296 | 3/2003 |
| JP | 5042218 | 2/1993 |
| JP | 6007440 | 1/1994 |
| JP | 6142114 | 5/1994 |
| WO | 1996005768 | 2/1996 |
| WO | 9725081 | 7/1997 |
| WO | 03000146 | 1/2003 |
| WO | 2010071416 | 6/2010 |
| WO | 2017066732 | 4/2017 |
| WO | 2018152225 | 8/2018 |
| WO | 2018204668 | 11/2018 |

OTHER PUBLICATIONS

Lacoste, "DSSS in a nutshell The Power of Patterns at Play", Circuit Cellar, Apr. 2020, #357, pp. 62-67.

Response to Communication filed in European Patent Application No. 18729820.3 dated Jun. 18, 2020.

Response to R161 communication filed in European Patent Application No. 18729820.3 dated Jun. 18, 2020.

International Search Report and Written Opinion issued in International Application No. PCT/US16/57264 dated Mar. 22, 2017.

Usubiaga et al., "Epidural Pressure and Its Relation to Spread of Anesthetic Solutions in Epidural Space", Anesthesia and Analgesia, vol. 46, No. 4, pp. 440-446, 1967.

Husemeyer et al., "Lumbar Extradural Injection Pressures N Pregnant Women", British Journal of Anaesthesia, 52, pp. 55-59, 1980.

Paul et al., "Extradural Pressure Following the Injection of Two Volumes of Bupivacaine", British Journal of Anaesthesia, 62, pp. 368-372, 1989.

Hirabayashi et al., "Effect of Extradural Compliance and Resistance on Spread of Extradural Analgesia", British Journal of Anaesthesia, 65, pp. 508-513, 1990.

Abstract of: Vas, "A study of epidural pressures in infants", Pediatric Anaesthesia, 11 (5), pp. 575-583, 2001.

Lechner et al., "Clinical results with a new acoustic device to identify the epidural space", Anaesthesia, 57, pp. 768-772, 2002.

Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.

Cohen et al., "Functional deficits after intraneural injection during interscalene block", Regional Anesthesia and Pain Medicine, vol. 35, No. 4, Jul.-Aug. 2010, pp. 397-399.

Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.

Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.

Steinfeldt et al., "Histological consequences of needle-nerve contact following nerve stimulation in a pig model", Anesthesiology Research and Practice, vol. 2011, Feb. 2011, 9 pages.

Steinfeldt et al., "Forced needle advancement during needle-nerve contact in a porcine model: Histological outcome", Anesthesia & Analgesia, vol. 113, No. 2, Aug. 2011, pp. 417-420.

(56) References Cited

OTHER PUBLICATIONS

Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.
Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.
Liu et al., "Incidence of unintentional intraneural injection and postoperative neurological complications with ultrasound-guided interscalene and supraclavicular nerve blocks", Anaesthesia vol. 66, 2011, pp. 168-174.
Abstract of: Bilbao et al., "Neurological complications associated with ultrasound-guided interscalene and supraclavicular block in elective surgery of the shoulder and arm. Prospective observational study in a university hospital", Rev Esp Anestesiol Reanim, vol. 60, No. 7, Aug.-Sep. 2013, pp. 384-391.
Widmer et al., "Incidence and severity of complications due to femoral nerve blocks performed for knee surgery", The Knee, Nov. 2012, 5 pages.
Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.
Kapur et al., "Neurologic and histologic outcome after intraneural injections of lidocaine in canine sciatic nerves", ACTA, Anaesthesiologica Scandinavica, vol. 51, 2007, pp. 101-107.
International Preliminary Report on Patentability issued in International Patent Application No. PCT/US16/57264 dated Apr. 17, 2018.
International Preliminary Report on Patentability for PCT/US2013/045142 Filed on Jun. 11, 2013.
Ghelber et al., "Identification of the Epidural Space Using Pressure Measurement . . . ", Regional Anesthesia and Pain Medicine, vol. 33, No. 4, Jul.-Aug. 2008, pp. 346-352.
Official Action issued in U.S. Appl. No. 11/208,400 dated May 29, 2008, 10 pages.
Iff et al., "The Use of an Acoustic Device to Identify the Epidural Space in Cattle", The Veterinary Journal, 187 (2011) pp. 267-268.
Iff, Isabelle, et al., "The use of an acoustic device to identify the extradural space in standing horses", Veterinary Anaesthesia and Analgesia, 2010, 37, 57-62.
Lechner et al., "Clinical Results with the Acoustic Puncture Assist Device, a New Acoustic Device to Identify the Epidural Space", Anesthesia Analgesia, (2003) pp. 1183-1187.
Lechner et al., "Thoracic Epidural Puncture Guided By an Acoustic Signal: Clinical Results", European Journal of Anaesthesiology, 21 (2004) pp. 694-699.
Lechner, T.J.M et al., "The use of a sound-enabled device to measure pressure during insertion of an epidural catheter in women in labour", Anaesthesia, 2011, 66, pp. 568-573.
Tsui et al., "Reduced Injection Pressures Using a Compressed Air Injection . . . ", Regional Anesthesia and Pain Medicine, vol. 33, No. 2, Mar.-Apr. 2008, pp. 168-173.
Extended European Search Report issued in EP Application No. 13813314.5 dated Feb. 18, 2016.
Examination Report issued in Australian Patent Application No. 2013287174 dated Oct. 26, 2016.
International Search Report and Written Opinion issued in PCT/US16/63861 dated Mar. 6, 2017.
Jonathan Dillon, "Embedded storage in disposable medical items"; Article posted on Aug. 1, 2011; https://www.electronicproducts.com/Digital_ICs/Memory/Embedded_storage_in_disposable_medical_items.aspx.
"Medical Device Sanity"; http://mdgoo.blogspot.com/2014/12/another-medical-device-supplier-with.html; published prior to Oct. 27, 2017.
Maxim Integrated Product Specification for DS28EC20 20Kb 1-Wire EEPROM; published prior to Oct. 27, 2017.

International Preliminary Report on Patentability issued in International Application No. PCT/US13/45142 dated Jan. 15, 2015.
Al-Aamri, et al., "Reliability of Pressure Waveform Analysis to Determine Correct Epidural Needle Placement in Labouring Women", Anaesthesia 2017, 72, pp. 840-844.
Cohen et al., "Epidural Block for Obstetrics: Comparison of Bolus Injection of Local Anesthetic with Gravity Flow Technique", Journal of Clinical Anesthesia, 9, 1997, pp. 623-528.
Cohen et al., "Extradural Block in Obstetric Patients: Review of Experience with Gravity Administration", Acta Anaesthesiologica Scandinavica, 35, 1991, pp. 676-679.
Dawkins, "The identification of the epidural space" Anaesthesia, vol. 18, No. 1, Jan. 1963, pp. 66-77.
McKendry et al., "Pressure Waveforms to Assess Epidural Placement: Is There a Role on Delivery Suite?", Anaesthesia, 72, 2017, pp. 815-820.
Ghia, et al., "Confirmation of Location of Epidural Catheters by Epidural Pressure Waveform and Computed Tomography Cathetergram", Regional Anesthesia and Pain Medicine, vol. 26, No. 4 (Jul.-Aug.), 2001, pp. 337-341.
Gong et al., "Pressure Waveform-Guided Epidural Catheter Placement in Comparison to the Loss-of-Resistance Conventional Method", Journal of Clinical Anesthesia, 26 (2014) pp. 395-401.
Hong et al., "Analysis of Epidural Waveform for Cervical Epidural Steroid Injections Confirmed with Fluoroscopy", An.md-journal.com, Hong and Jung Medicine (2018) 97:13, 4 pages.
Lennox et al., "A Pulsatile Pressure Waveform Is a Sensitive Marker for Confirming the Location of the Thoracic Epidural Space", Journal of Cardiothoracic and Vascular Anesthesia, vol. 20, No. 5 Oct. 2006, pp. 659-663.
Leurcharusmee et al., "Reliability of Waveform Analysis as an Adjunct to Loss of Resistance for Thoracic Epidural Blocks", Regional Anesthesia and Pain Medicine, vol. 40, No. 6, Nov.-Dec. 2015, pp. 694-697.
Suwa et al, "Pressure-Guided Method for Identification of the Epidural Space in Children", Anesthesiology, vol. 89, No. 2, Aug. 1998, pp. 546-548.
Hsu et al., "The Frequency and Magnitude of Cerebrospinal Fluid Pulsations Influence Intrathecal Drug Distribution: Key Factors for Interpatient Variability", www.anesthesia-analgesia.org, vol. 115, No. 2, Aug. 2012, pp. 386-394.
Wagshul et al., "The pulsating brain: A review of experimental and clinical studies of intracranial pulsatility", http://www.fluidsbarrierscns.com/content/8/1/5, 2011, 8:5, 23 pages.
Hettiarachchi et al., "The Effect of Pulsatile Flow on Intrathecal Drug Delivery in the Spinal Canal", Annals of Biomedical Engineering, vol. 39, No. 10, Oct. 2011, pp. 2592-2602.
Hilber et al., "Asystematic review of the diagnostic accuracy of epidural wave form analysis to identify the epidural space in surgical and labor patients", http://www.minervamedica.it, Minerva Anestesiologica, Apr. 2019, 85(4), pp. 393-400.
Iff et al., "The Use of an Acoustic Device to Identify the Extradural Space in Standing Horses", Veterinary Anaesthesia and Analgesia, 37 (2010) pp. 57-62.
Hungarian Novelty Report for Application No. P 04 00176.
NL Search Report, NL 2002708, dated Oct. 9, 2009.
PCT International Prelminary Report on Patentability, PCT/NL2010/000061, dated Oct. 4, 2011.
PCT International Search Report, PCT/NL2010/000061, dated Aug. 23, 2010.
International Search Report and Written Opinion issued in International Application No. PCT/US18/31096 dated Sep. 10, 2018.
Ross et al., "Pressures of Injection in a Cadaver Model of Peripheral Nerve Blockade", Journal of Anesthesia & Clinical Research, 2014, vol. 5, Issue 10, 4 pages.
Product brochure "PAJUNK: NerveGuard Automatic system for injection pressure limitation" (XS200192B) dated Jan. 2017, 4 pages.
https://www.dermaqueen.co.ki7, published prior to Feb. 15, 2017.
http://www.intranixtech.com/myoguide-system/, published prior to Feb. 15, 2017.
http://www.anteis.com/AestheticDermatology/injectionsystem.php, published prior to Feb. 15, 2017.

(56) References Cited

OTHER PUBLICATIONS

International Search Report & Written Opinion issued in International Application No. PCT/US13/45142 dated Sep. 10, 2013.
International Preliminary Report on Patentability issued in International Application No. PCT/US06/29091 dated Feb. 28, 2008.
Gadsden, et al., "High Opening Injection Pressure Is Associated With Needle-Nerve and Needle-Fascia Contact During Femoral Nerve Block", Regional Anesthesia and Pain Medicine, vol. 41, No. 1, Jan.-Feb. 2016, pp. 50-55.

* cited by examiner

METHOD AND APPARATUS FOR PERFORMING A PERIPHERAL NERVE BLOCK

PRIORITY CLAIM

This application is a U.S. National Stage of International Application No. PCT/US18/31096 filed on May 4, 2018, which is a continuation-in-part of claims priority U.S. patent application Ser. No. 15/587,119 filed May 4, 2017. This application also claims priority to U.S. Provisional Application No. 62/501,546 filed May 4, 2017. The entire disclosure of each of the foregoing applications is hereby incorporated herein by reference.

FIELD OF THE INVENTION

The present invention relates generally to improvements to the delivery of drugs, particularly to systems for subdermal injection/aspiration. More specifically, the invention provides a method and apparatus for distinguishing between different needle tip locations when performing a Peripheral Nerve Block or advancing any medical device is in the vicinity of a nerve, plexus or nerve root.

BACKGROUND OF THE INVENTION

A peripheral nerve block (PNB) is used for anesthesia, postoperative analgesia, and diagnosis and treatment of chronic pain syndromes. Peripheral nerve blocks may also improve acute pain management and patient disposition even when used only as adjunct techniques. An objective of the PNB regional anesthesia technique is to identify the target nerve and position a hollow-bore needle in a defined proximity relative to the targeted nerve without causing untoward reactions such as structure damage to the nerve or causing excessive pain to the patient. Despite the increased use of ultrasonography to aid visualization of the block needle, target nerves and local anesthetic spread, the incidence of intra-neural injection during USG PNB has been reported to be higher than previously expected; even experts fail to detect 1 in 6 intra-neural needle tip placement before injection. The use of ultrasonography has not reduced the incidence of Postoperative Neurologic Symptoms (PONS) when compared with landmark nerve stimulation (NS) guidance. One day after PNB procedures, neurological symptoms such as paresthesia or residual blockade have been reported to be present in up to 19% of patients, persisting in approximately 3% of patients during the first few months. The incidence of long-term (6-12 months) PONS also remains between 2 and 4 per 10,000 PNBs.

Referring to FIG. 1, a schematic description of the microanatomy of the peripheral nervous system is provided. The basic building block to both the central and peripheral nervous system is the single cell unit commonly known as is the axon. The brain and central nervous system are composed of millions of axons. Branching off the central nervous system of the brain stem and spinal cord is a collection of highly organized axons forming a network of sensory and motor pathways via the axons. At the emergence of the spinal canal, this network of pathways is collectively known as the peripheral nervous system.

In the peripheral nervous system, each individual axon is surrounded by supporting connective tissue called the endoneurium. Contained within the endoneurium are small blood vessels (capillaries and venuoles) providing nutrients to these axons. Axons are collectively formed into highly organized, packed bundles that are surrounded by a thin but dense multi-layered connective tissue sheath that surrounds and forms a membrane structure called the perineurium. The perineurium provides a dense protective layer that is both a physical and chemical barrier, providing a degree of protection for the axons and endoneurium. This barrier is akin to the blood-brain barrier.

This discrete unit of the endoneurium and perineurium is called a peripheral nerve fascicle. When fascicles coalesce together they form fascicular bundles embedded in epineurium, which is a connective tissue sometimes referred to as inner or interfascicular epineurium. The multiple groups of fascicles are embedded in a non-uniform matrix of connective tissue (fibro-adipose tissue) and mid-size vessels that are loosely arranged together with an outer perimeter of dense connective tissue. The bundled fascicular structures collectively surrounded by this additional densely, more highly organized layer of fibrous tissue, houses the peripheral nerve contents and is known as the outer epineurium.

The outer epineurium connects the outer layer to the neighboring structures. A loose connective tissue fills the space between the nerve and the surrounding tissue in connection with the outer epineurium. There is thus an additional multi-layer boundary beyond the outer epineurium that runs along the entire trajectory of the nerve and is composed of an extra-neural connective tissue known as the paraneurium, (mesoneurium or gliding apparatus). The paraneurium is a distinct multi-layer functional structure that enables the nerve to glide relative to other anatomic structures during muscular-skeletal movements.

To aid in locating a nerve branch, electrical stimulation may be utilized. Introducing an electrical current stimulation to the body has the ability to elicit an indirect excitation of both the sensory and motor components of a nerve. This was found to provide a visual muscle contraction and an electrical paresthesia when the electrical stimulation was applied on motor and sensory axons respectively. Modulating the current charge (intensity and duration) and frequency lead to contraction and relaxation of muscle groups innervated by a nerve branch. However, this use of an indirect electrical charge to produce a nerve reaction to a specific nerve has not achieved widespread adoption because of several deficiencies, including:

An inability to accurately modulate an applied electrical charge at a given distances to the surface of a nerve branch has made nerve stimulation limited in the identification of a specific nerve branch when using nerve stimulation as the primary means of nerve branch location. A variety of charge intensities are recommended at specific distances when approaching the nerve branch. However, needle tip to nerve distance and current intensity noted by a visual muscle twitch reaction does not necessarily correlate. During the procedure, a nerve stimulation (NS) to a lower electric charge does not necessarily mean the needle is closer to the surface, at an extra-neural position or located within the nerve. Similarly, nerve stimulation to a greater current charge does not necessarily mean the needle is a greater distance to the intended nerve branch. The basic principles of electric nerve localization—current intensity being proportional to the needle-nerve distance, stimulating currents between 0.1 and 0.4 mA linked to distances of <2 mm—have been shown to be overgeneralizations. Electric current conduction, propagation, and initiation of a motor response are influenced by anatomic structures, such as the arrangement of muscles, connective tissues, and resistive barriers in the vicinity of the needle. Electric nerve stimulation is indirect localizing method, and not a precise guidance for needle placement. However, a motor response at a low current charge is specific of the needle tip location in the vicinity of a bundle of axons, An inability to set the appropriate current charge for a nerve stimulation at defined distance from the outer surface of the fascicle, i.e., Extra-Fascicular. It is more concerning if a high current charge is utilized in the vicinity of a fascicle or Intra-fascicularly, as it may cause a forceful response by the patient. Finally, there is an inability to determine what appropriate charge should be applied for a specific distance from the fascicle and or the nerve. Needle-nerve contact or intra-neural needle placement often fails to promote motor response at a low current charge (0.3 to 1 mA), a lack of sensitivity confirmed in animal and human studies. However, an evoked motor response (EMR for current intensity below to 0.2 mA is known to be specifically predictive of an intra-neural needle position prior to any injection. Moreover, an evoked motor response (EMR for current intensity below to 0.1 mA is known to be specifically predictive of an intra-fascicular needle position prior to any injection Confounding variables can make the use of nerve stimulation a non-specific technique. These are related to anatomic variations within a given patient as well as anatomic variation between different patients. The body is comprised of a variety of tissue types composed of water and collagen, adipose tissue (fat), muscle, fluids (blood, lymph, and interstitial liquid), bone, cartilage, etc. Each of these tissues types provides a different resistance and/or capacitance to a charge when electrical current is applied at a given distance to the intended target. As a result, the current charge needed to stimulate a nerve or a fascicle varies non-linearly with the distance, varies at injection of fluids, tissue density and/or by mechanical pressure of the needle tip on a fascia.

The variables of current charge (intensity) and tissue impedance to the electric stimulus have made it difficult to standardize a technique to enable precise needle to nerve distance and relationship respective to the layers of a specific fascicle, nerve and/or plexus. Nonetheless, an EMR at a very low current has been found to be highly specific of intra-neural location of the needle tip.

Injection pressure monitoring (IPM) is highly sensitive to detect a peak pressure as soon as the needle tip encounters a dense connective tissue. However, IPM is not specific of the nature of the dense connective tissue. A low-pressure range is specific of a low-density tissue loose connective tissue such as fat, interstitium, or muscle. A high-pressure range is specific of a dense connective tissue (fascia, tendon, nerve . . . ) but a pressure signature is not highly specific of the tissue type. For instance, a tendon and a nerve have similar aspect on an ultrasound image. Indenting the surface layer of the tendon and the nerve may produce similar high peak pressure. Similarly, IPM cannot differentiate paraneural from extra-neural interstitium.

| Tissue density | Dense | Intermediate | Loose |
| --- | --- | --- | --- |
| Evoked motor response to NS | Perineurium Outer epineurium | Inner epineurium | paraneurium |

| Tissue density | Dense | Intermediate | Loose |
| --- | --- | --- | --- |
| no motor response | Tendon Muscle fascia | Intermuscular fascial plane | Subcutaneous fat Intermuscular, perivascular interstitium |

SUMMARY OF THE INVENTION

Ultrasonography allows simultaneous visualization of the target nerve, needle, local anesthetic solution and surrounding anatomical structures. Nevertheless, ultrasonography as a sole method of monitoring may not reliably prevent neurologic injury. Nerve stimulation has low sensitivity to differentiate relative needle tip position to the nerve layers but is highly specific of neural tissue nearness. Injection pressure monitoring is sensitive for detecting high injection pressure in dense tissues such as needle-nerve contact or intra-fascicular injection. The present invention provides combines these monitoring options in a multimodal approach, to decrease the risk of neurologic complications when performing PNBs.

According to one aspect, the present invention combines IPM sensibility and NS specificity to differentiate different needle tip locations during peripheral nerve blockade, to detect nerve puncture and to help avoid intra-neural injection. The IP can be continuously monitored during the procedure of needle guidance to the nerve, so that when the pressure exceeds a threshold the electric stimulation is increased. The lack or occurrence of EMR indicates the absence or presence of the nerve at the needle tip, respectively. The occurrence of a pressure peak and a low intensity at EMR indicates the vicinity of the nerve. A pressure peak and very low intensity stimulation with an associated EMR indicates a nerve puncture or intra-neural needle tip location.

An additional aspect of the present invention provides a mechanism to assist with nerve detection, decrease the occurrence of intra-neural injections and avoid injection in a dense connective tissue close to or particularly into the fascicles. Additionally, another aspect of the present invention enables one to use pressure sensing to differentiate between dense (low compliance) tissues such as neural (neural fascicle) versus connective tissues (muscle fascia).

Another aspect of the current invention is a system in which continuous infusion of fluid medium at a fixed flow-rate is provided so that the hydraulic pressure can be precisely measured by an in-line pressure sensor. The ionic properties of fluid medium influence the transmission of an electrical current charge thru the tissues. The solution injected can be ionized (saline or local anesthetic) or non-ionized (dextrose in water). The solution may be dispensed through a disposable syringe and tubing in a uniform way to the tip of the needle for the purpose of nerve stimulation conduction. An ionic solution decreases the impedance so that electrical current charge can more effectively be dispersed through the tissues; the voltage is less for the same current intensity (Ohm's law) so that the stimulating current is less painful and the electric field reduced.

A further aspect of the current invention is a system that provides an ability to enhance ultrasound visualization at the injection site by providing an increased fluid flow rate at appropriate needle tip location. The increased fluid flow allows the tip of the needle to be more easily identified during the advancement of a needle through tissues when performing a peripheral nerve block, thus aiding in the prevention of needle tip placement, particularly into the nerve.

Another aspect of the current invention is controlling the electrical stimulation based on signals received regarding fluid pressure in the needle.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
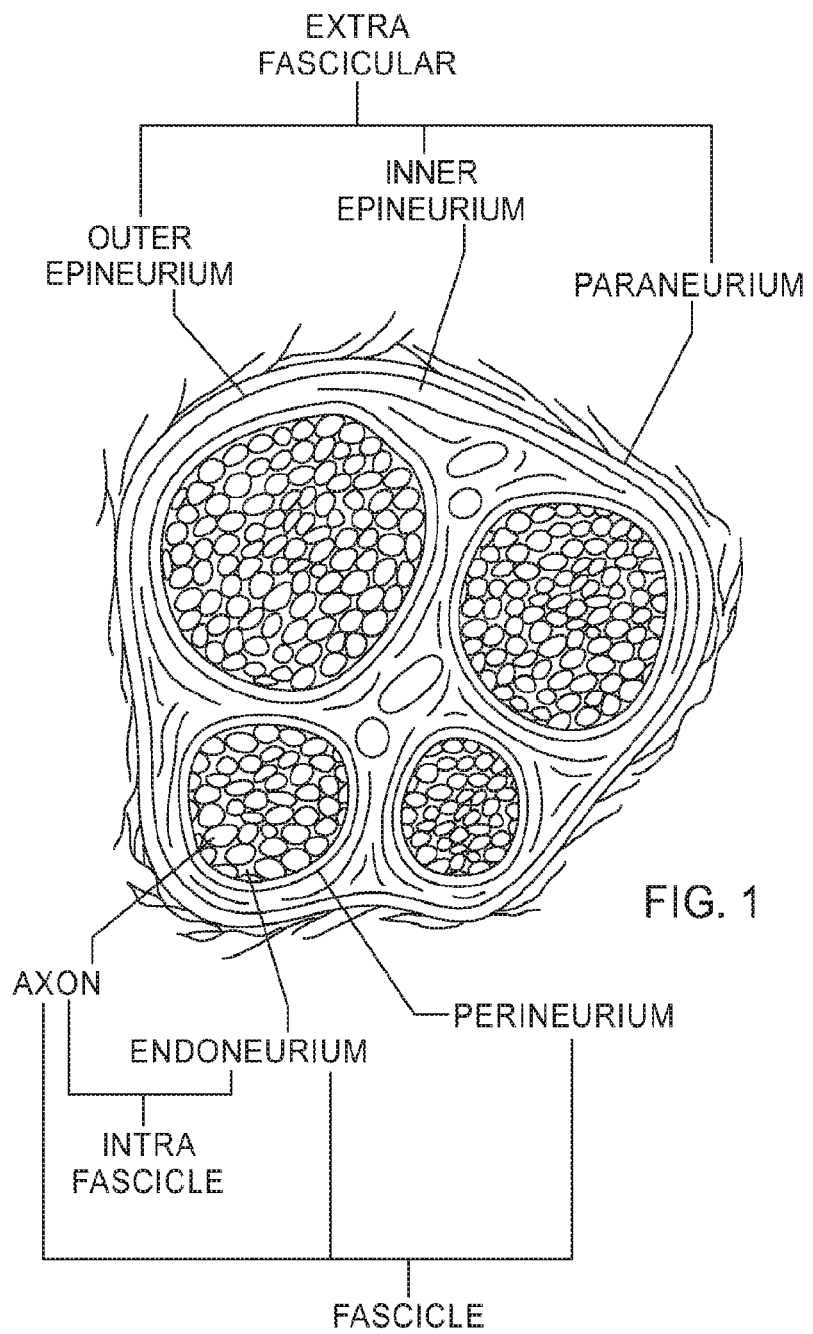
FIG. 1 is a cross-section view of a fascicle of nerve fibers.
Figure 2:
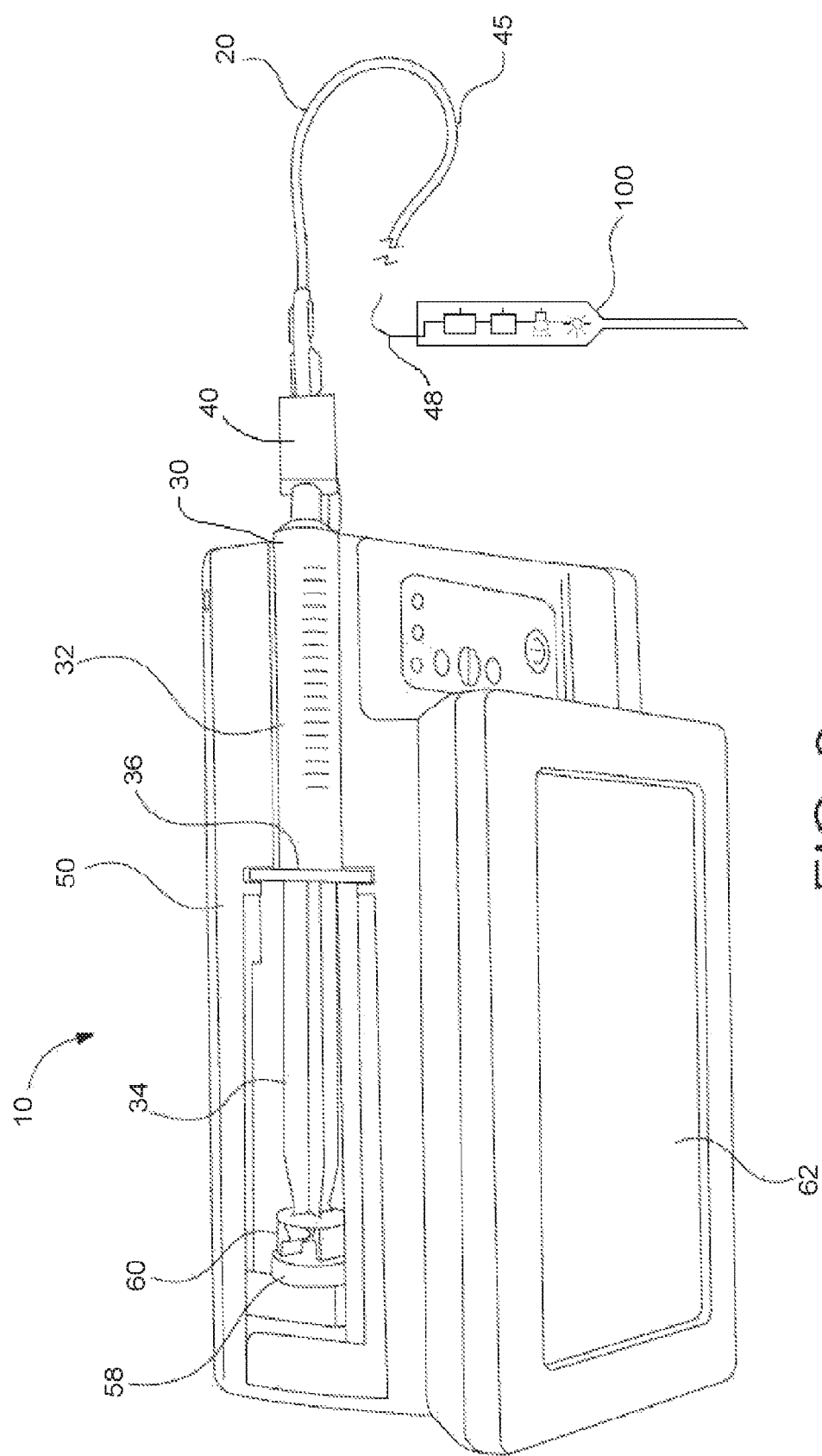
FIG. 2 is a perspective view of a drug delivery system.
Figure 3:
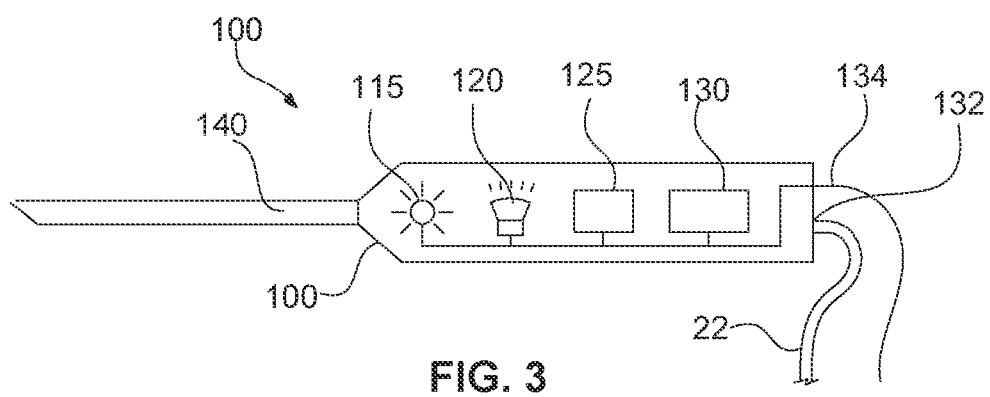
FIG. 3 is an enlarged side view of a handpiece of the drug delivery system illustrated in FIG. 2.

Referring now to the drawings, in general and to FIGS. 1-3 specifically, a drug infusion system is designated generally 10. The system 10 includes an injection assembly 20 and a computer-controlled drug delivery instrument 50, referred to as a drive unit. The injection assembly 20 includes an insertion needle 140 configured for insertion into a mammalian subject. The injection assembly 20 is connected with the drive unit 50, which controls the flow of fluid to the injection assembly during use. The system 10 also includes one or more output mechanisms that provide data to the medical professional during a procedure to assist in proper placement of the needle in the subject.

The system 10 is operable to determine the location for an intra-fascicular needle location. The system is also operable to deliver therapeutic medication to an extra-fascicular needle location. The medication may include, but is not limited to local anesthetic solutions, such as, cortico-steroids, hydroxyapatite, joint replenishment drugs, sclerosing agents and other drugs that are typically injected into a fluid-filled tissue space for therapeutic purposes. The system is also operable to measure the hydrostatic pressure in a tissue compartment such as in a muscle or in the interstitium.

An intra-fascicular needle location is one in which the tip of the needle penetrates through the perineurium so that the needle tip is located inside the fascicle. An extra-fascicular needle location is a position in which the needle is anywhere outside the perineurium of an individual fascicle, which may include inside the epineurium or the paraneurium thereby defined as completely extra-neural or in the surrounding structures of the nerve.

Irreversible damage can occur to a nerve when the needle tip is both embedded into a fascicle and then fluid under hydrostatic pressure produces changes to the neural and vascular tissues within the fascicle. This occurs because the outer layer of the fascicle is a protective layer of a relatively non-compliant, rigid protective structure. This protects the basic components of the nerve, the axons, which are densely packed within the fascicle. In other words, the fascicle represents a densely packed arrangement with a thick protective shell. The fascicle does not readily deform by either expanding or contracting. Therefore, tissue compliance to an inflow of fluids is extremely low and/or non-existent. Needle penetration into the fascicule may not necessarily cause the ultimate damage to the axon units, but the combined effect of needle penetration and increased pressure inside the fascicle from the infusion of fluids inside the fascicle can produce damage to the capillary bed. Additionally, fluid pressure-induced strangulation of the microcirculation of the axons impedes short-term nutrient replenishment after such physical trauma thus leading to initial necrosis. The cascade from necrosis leads to an inflammatory response in an effort to initiate a wound healing from the initial pressure-induced trauma further advancing or cascading potentially toward irreversible damage.

However, there are instances in which intentional intra-fascicular needle placement is desirable and required. Such instances include unresolved phantom pain after a limb is removed. Additionally, hyperactive neural stimulation of a particular limb may sometimes lead to retractable pain and is another circumstance in which intentional intra-fascicular needle location and delivery of agents is required. Accordingly, the system 10 and its use may provide an alternative method and apparatus for discriminating between the extra-fascicular and intra-fascicular location of a needle.

Injected fluid disperses through tissue at different rates. As a result, the fluid pressure varies. Therefore, this fluid pressure (or an internal pressure related to the resistance pressure of a tissue) is indicative of, and may be used to identify several types of tissues densities.

There are also instances in which a practitioner desires to inject a drug into dense tissues such as the fascia of muscle, tendon or other bodily tissue that is to be identified as a tissue that is not composed of neural tissues.

The system 10 enables a practitioner to accurately identify fluid-filled tissue space while limiting the placement of drugs into non-targeted tissues. This is performed for both diagnostic and therapeutic procedures. The system 10 utilizes the pressure of a fluid as it flows from a needle or catheter following placement of the needle/catheter within the tissue in order to identify the accuracy of placement and to monitor the placement during an injection or aspiration. System 10 may utilize a continuous flow of fluid at what is considered a slow flow-rate that is defined as a constant flow-rate between 0.01 mL/sec to 0.20 mL/sec. The continuous flow of fluid maintains a constant column of fluid that may enable a virtually instantaneous reaction time to pressure changes within the tissues to be detected.

Specifically, the system 10 includes one or more output mechanisms for providing audible and/or visual feedback of the detected fluid pressure in the insertion needle. The operator uses the feedback as guidance during the placement of the insertion needle. As shown in FIG. 2, the first output mechanism may be a video display screen, such as an LCD display for displaying data to aid the operator. Additionally, a second output mechanism may also be provided. For example, the second output mechanism may be a speaker for providing an output signal.

Injection Assembly

Referring to FIG. 2, the system 10 includes an injection assembly 20 cooperable with a drive unit 50 during a drug infusion procedure. The injection assembly includes a syringe 30, a handpiece 100, a fluid line 45 connecting the syringe with the handpiece and a cable 48 providing an electrical connection between the handpiece and the drive unit 50. The assembly further includes a needle 140 releasably connected with the handpiece 100.

Various elements of the injection assembly may be disposable, such as the syringe 30, the fluid line 45, the handpiece 100 and/or the needle 140. Alternatively, the elements may be re-useable. Accordingly, various elements of the injection assembly are releasably connectable. For instance, the fluid line 45 may include a fluid connector at each end. The fluid-tight connectors may be any of a variety of connectors. One exemplary connector is a Luer connector or NRFit for regional anesthesia. At the first end, the fluid connector sealingly connects with the syringe and at the second end the fluid line sealingly connects with the handpiece 100. Alternatively, the fluid line 45 may be fixedly connected with the rearward end of the handpiece 100. In either embodiment, the handpiece 100 and the syringe are in fluid communication to provide a flow of fluid from the syringe to the handpiece. Alternatively, another connector is added along the fluid line; this connector may be used to provide fluid from another syringe connected to a tubing and a unidirectional valve and may be manually operated to inject fluid such as local anaesthetic. Specifically, a secondary syringe filled with a therapeutic agent can be administered once the target location has been identified or during the entire procedure.

The syringe 30 may be any of a variety of hypodermic syringes and the length and gauge may vary depending on the intended use. The syringe 30 includes a barrel 32 for holding a volume of medicament and a plunger 34 slidable within the barrel to draw fluid into or eject fluid from the barrel. The syringe 30 preferably also includes flanges 36 projecting outwardly from the barrel. The flanges operate as finger flanges to facilitate displacement of the plunger into the barrel.

The injection assembly 20 also includes a pressure sensor 40 for detecting fluid pressure in the injection assembly. The pressure sensor may be disposed in one of several locations to measure a pressure that correlates with the fluid pressure at the tip of the needle 140. Alternatively, rather than or in addition to an in-line pressure sensor, the pressure sensor may be a force sensor located within or connected to the thumb plate that drives the syringe plunger 58 or a force sensor that is internal to the drive unit 50 that measures the force applied to the syringe plunger. Such a force sensor detects the force required to inject the fluid, which is related to the fluid pressure in the needle. Using such a sensor, the detected force is converted to a pressure value by a calculation via the processor. In the present instance, the pressure sensor 30 is an inline fluid pressure sensor attached to the syringe 30 between the syringe and the tubing 45. In this way, the pressure sensor 40 senses the fluid pressure as the fluid exits the syringe and enters the tubing 45 to which the insertion needle 140 is connected. Similarly, the in-line pressure sensor can be interposed between the tubing and the needle.

The injection system 10 may also include a re-useable handpiece 100 to which the needle 140 is attached. As shown in FIG. 2, the insertion needle 140 is connected to the forward end of the handpiece and the tubing 45 is connected to the rearward end of the handpiece. The handpiece 100 may be configured to provide electrical stimulation as discussed further below.

The injection assembly 20 may be manually operated to inject fluid. However, in the present instance, a computer-controlled drug delivery system 50 controls the flow of fluid from the injection assembly as discussed further below. An electrical cable 48 connects the pressure sensor 40 with the drug delivery system 50 so that the drug delivery system can monitor and, if desired, vary the flow of fluid from the syringe in response to the data from the pressure sensor 40. The pressure-transducer 40 may be connected inline between the forward end of the cylinder of syringe 30, and the first end of tubing 45. One exemplary connection is a Luer connection for connecting the pressure-transducer 40 to the tip of the syringe. The connection may be fixed by a threaded connection and/or an irreversible threaded connection, such as a LuerLock or such as NRFit for regional anesthesia. Alternatively, the pressure transducer 40 may be permanently fixed to the syringe by plastic welding or chemical binding, such as adhesive. In this way, the instantaneous, actual fluid pressure in the drug delivery line 45 is sensed and used by the instrument, thereby providing a close approximation to the actual, instantaneous fluid pressure at the point or tip of the needle 140, and therefore, at the location in the patient's body where the needle tip is located. The electronic pressure-transducer 40 provides pressure data via an electronic data cable that is connected directly to the central unit 50 to collect the pressure measurements.

The electronic pressure transducer 40 can be any of various pressure sensors. One type of exemplary sensor is a piezoelectric pressure sensor, such as sensors available from Merit Medical Systems, Inc. such as the Meritrans® Pressure Transducer item MER212.

Automated Fluid Delivery System

As described above, the system 10 may include a fluid delivery system 50 for providing a controlled flow of medication to the injection assembly 10. Preferably the fluid delivery system is an automated system and in the present instance is a computer controlled fluid delivery system referred to as a drive unit 50.

Figure 4:
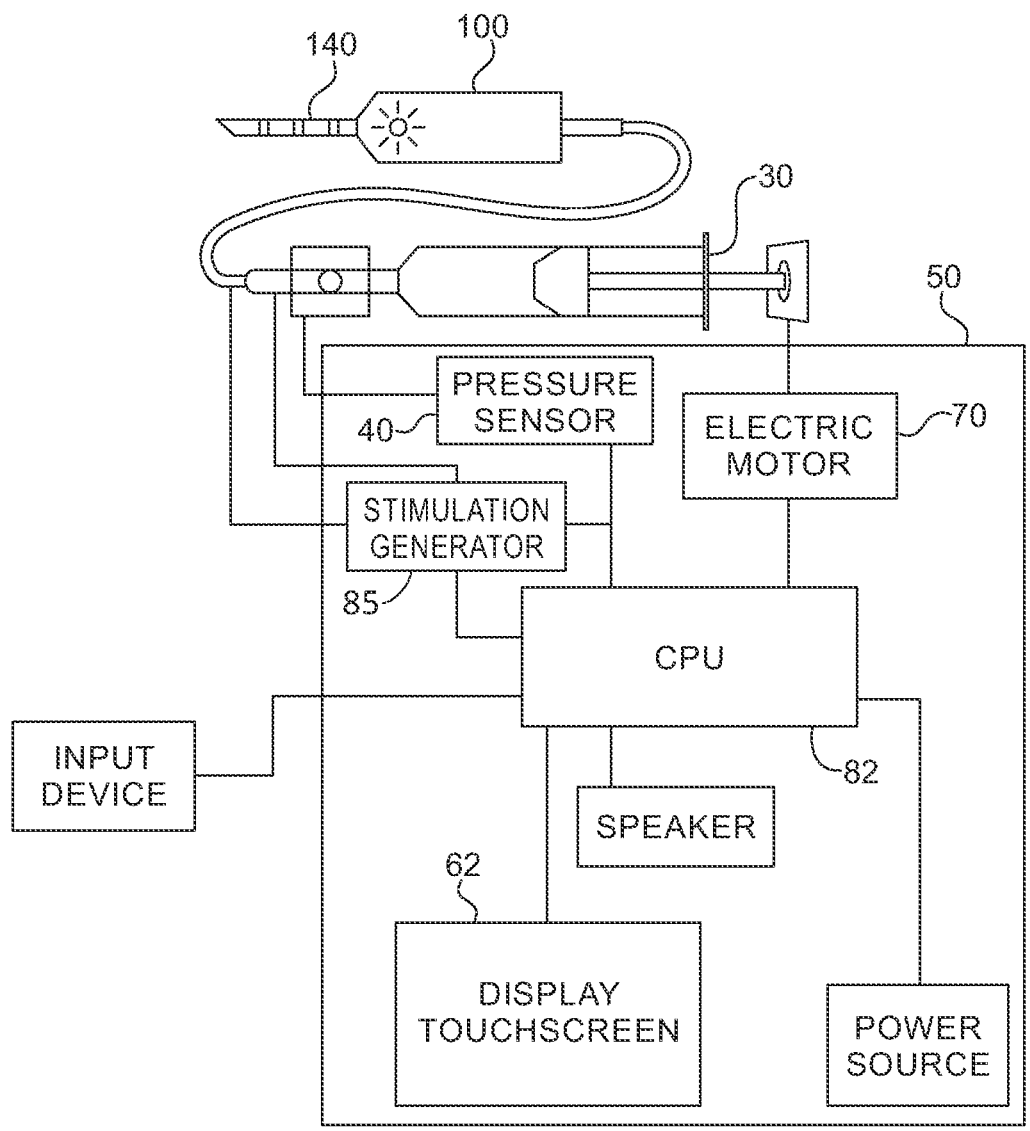
FIG. 4 is a diagrammatic view of an injection device of the drug delivery system illustrated in FIG. 2.

Referring to FIGS. 2&4, the drive unit 50 is designed to work in connection with an injection element, such as syringe 30. The drive unit 50 may include a cradle configured to receive the syringe 30 and a clamp for retaining the syringe in the cradle. The drive unit 50 includes a drive element 58 operable to drive the plunger in the syringe to expel fluid from the syringe. The drive unit 50 controls the displacement of the drive element 58 thereby controlling ejection of fluid from the syringe. In the present instance, the drive element may include a motor 70 driving an arm 58 having a clamp with a plurality of fingers that releasably engage the plunger 34. Driving the motor in a first direction drives the arm 58 forwardly to advance the plunger 34, thereby expelling fluid. The CPU 82 of the drive unit provides signals to the motor to control operation of the motor.

The drive unit 50 is operable to provide constant or variable fluid flow. In the present instance, the drive unit may provide a continuous fluid in response to signals received from the electronic pressure-transducer 40, which continuously senses the pressure of the fluid during an insertion/injection procedure. Based on a pre-determined pressure, the drive unit 50 may stop the flow of fluid when the detected pressure exceeds a pre-defined threshold. The pre-defined threshold may be set by the practitioner and stored in a memory 80 of a microprocessor or computer 82 of the electronics in drive unit 50. Similarly, based on a pre-determined pressure, fluid-flow will resume when the fluid pressure falls below a pre-determined pressure and will continue to flow while the pressure remains below the threshold. The same pre-determined pressure may be used to control the stopping and re-starting of the fluid flow. In such case, as fluid initially enters the tissue the pressure will build to a pre-determined level and then stop until once again the pressure drops below this pre-determined level. Once the fluid pressure falls below the pre-determined level, the fluid-flow will resume and be maintained on a continuous basis. In this way, the flow of fluid may start and stop during the procedure creating an interruption of fluid flow once a specific pre-determined pressure is detected The system may include pre-defined pressure thresholds used to control the flow of medication from the syringe 30 during the procedure. This enables a clinician to selectively inject drugs into specific sites and intended tissues for diagnostic and therapeutic procedures. Pre-selected maximum allowable pressure limits and/or flow rates are stored in memory 80 and define either the maximum recommended pressures that patients usually tolerate, or other criteria. As the pressure approaches this limit, a visual and/or audible alarm is generated for the clinician, i.e. on screen 62 and via speaker 84 that is activated by data from the microprocessor 82. In addition, data descriptive of the whole injection process is stored for future analysis in memory 80.

The system 10 may directly measure the fluid pressure in the injection assembly 10 or the system may measure a characteristic indicative of the fluid pressure in the injection assembly. For instance, the pressure may be measured by detecting the pressure resistance measured during infusion. The pressure resistance measured is converted into a visual signal on a continuous basis during the insertion procedure. The flow rate of medication during the procedure may be based on the fluid pressure detected in real time during the procedure. Therefore, the flow rate of the medication may be variable and may be dependent on the pressure in the system. In this way, the fluid pressure may be the primary controlling variable of the system.

One feature of the present system is the ability to detect minute changes in pressure at the needle tip while a needle is placed within the patient's tissue. This ability to detect subtle pressure changes is based upon a constant movement of fluid into the tissues under controlled conditions thus enabling one to identify and or avoid undesirable locations based on pressure within the tissue. The system detects these minute changes in pressure in real-time and dynamically when a continuous flow of the fluid is used. This continuous flow is coordinated with a pre-determined maximum pressure used by the system to stop the flow of fluid at a pre-determined pressure limit to avoid damage to these tissues. With a constant flow of fluid the head pressure provides the needed resistance within the tissues to enable subtle changes in the tissue density and compliance to be detected on a virtually instantaneous basis.

The flow-rate, therefore, becomes a second variable that is modulated within a pre-determined range in order to maintain the desired fluid-flow. In one specific embodiment, the fluid flow is stopped when the pressure exceeds a pre-determined threshold (maximum pressure). The flow-rate, as a second variable, may be limited so that fluid injections are not unduly rapid under low pressure conditions. It is contemplated that the relationship between pressure and fluid flow rate may either be binary or continuous. A binary relationship exists when the injection device is configured to deliver fluid at a single, pre-determined flow rate for any pressure less than the pre-set maximum. Thus, the fluid flow is either on or off based on whether or not the pressure exceeds the threshold. Alternatively, the flow rate may be modulated as a function of pressure. In this case, flow rate will be reduced as the maximum pressure is approached and increased as the pressure drops. Optionally, the flow rate may be limited to a first pre-set maximum pressure and a flow rate resumes at a second distinct pre-determined pressure.

As mentioned above, the system 10 may include a mechanism for displaying relevant injection data including, for example, instantaneous flow rates, pressures, and injection amounts upon a screen 62 of the drive unit 50. In addition to the visual feedback, the system may include an element for providing audible feedback to the operator. For instance, the system may include a transducer that provides audible feedback such that the audible signal varies as the pressure varies. Further still, the system may include an element for providing an audible alert or indication signal if the pressure exceeds certain predefined levels. The system may also include a mechanism for recording the relevant injection data for subsequent analysis after the procedure is performed. For instance, the system may include a non-volatile electronic storage medium, such as a hard drive, flash drive, optical drive or other medium for storing electronic data and also may include a network connection to provide the ability to connect to the hospital or office computer system for storage in real time in the patient record. In this way, the system may enable the transfer of the data generated from the PNB injection automatically and efficiently.

All measurements and information may be presented to the clinician in "real-time" so that the clinician may determine whether the injection is being delivered to the intended location and/or correct tissues and may modify the injection technique accordingly. In addition, the measurements may be recorded for later review and documentation of the clinical event.

It is also contemplated that multiple syringes driven by separate syringe plungers may be used to allow multiple drugs to be injected as well as a second syringe drive that does not required a pre-determined pressure to be reached for any said purpose. The second drive can be programmed on a specific flow-rate to allow infusion of a drug such as local anesthetic and other therapeutic drugs into a variety of tissues.

In yet another embodiment the device may contain two distinct syringe drives in which both are capable of modulation based on fluid-pressure as previously herein described.

Electrical Stimulation

The system may also include an electrical stimulation element for providing electrical nerve stimuli to a target tissue in a patient. The electrical stimulation element is a conductive element connected with the handpiece 100 or an insulated needle used for peripheral nerve blockade. The electrical stimulation element is operable to provide an electrical charge of low intensity (i.e. approximately 0.10 mA up to approximately 6.0 mA), short duration (i.e. pulses of approximately 0.05 to 1 Ms) and frequency 1, 2 to 4 Hertz, and a maximum voltage (100 volts). The electronic stimulation elements provide the stimuli for a short time (i.e. approximately 1-10 seconds) at constant, incremental or decremental current charge The electric stimulator may be an external element or an internal element. For example, FIGS. 2-4 illustrate an embodiment that incorporates external electric stimuli. A conductive element such as an electrically conductive cable 48 interconnects the handpiece 100 with a stimuli generator 85, so that electrical stimuli are transmitted to the handpiece from the stimuli generator. In turn, the handpiece is connected with an element configured to deliver the electrical charge to the tissue. For instance, the needle 140 may be formed of electrically conductive material and the handpiece may include a connection with the needle providing an electrical pathway from the conductive element 48 to the needle. Alternatively, a conductive element, such as a wire, may extend along the length of the needle and the needle may be electrically insulated from the needle. For example, the needle coating may be formed of electrically insulative material. An example of an external electric stimulation element is the insulated needle sold under the trade name "Stimuplex®" or the over the needle catheter sold under the trade name "Contiplex® C" by B. Braun Medical Inc. of Bethlehem, Pa.

The system may utilize internal electric stimuli rather than the external electric stimuli described above. For example, the fluid injected from the syringe may be an ionic solution capable of conducting electric stimuli. A conductive element may be interconnected with the fluid within an insulated needle. The needle may be constructed from a variety of non-conductive materials. For instance, the conductive element may project into the fluid path at some point between the syringe 30 and the needle 140. For example, the conductive element may impart the electric stimuli into the fluid at the rearward end of the handpiece 100. If the electric stimuli are imparted to the tissue via the fluid, the needle 140 may be electrically insulated to minimize any drain or disbursement of the electric charge through the sidewalls of the needle.

As shown in FIGS. 2&4, the electrical stimulation element is connected with an electric stimuli generator 85, which is an electrical source operable to provide an electrical charge or pulse to the stimulation element. The stimuli generator may be incorporated into the drive unit 50 as shown in FIG. 4. In such an arrangement, the stimuli generator 85 is connected with the CPU of the drive unit so that the CPU provides electric signals to control the operation of the stimuli generator. Alternatively, the stimuli generator may be a separate element having a separate power source and separate control.

The evoked electric motor response (EMR) can be visually assessed by the operator or detected by accelerometry, electromyogram, or any other monitoring of nerve stimulation and/or muscle contraction leading to control the nerve stimulation and/or the flow rate and/or warning signals.

Calculation of Fluid Pressure at the Exit of the Needle

As discussed above, the fluid pressure may be used to control operation of the system 10. For instance, the system may provide a signal to the operator when the fluid pressure exceeds a threshold, thereby indicating that the needle may be located intra-fascicularly or indenting the outer epineurium of the nerve. There are several methodologies for calculating the fluid pressure at the exit of the needle.

A pressure sensor may detect the fluid pressure in the injection assembly 100. For example, as discussed above the pressure sensor may be an in-line pressure sensor, such as that available by Merit Medical part #0001. Alternatively, a pressure sensor internal to the drive unit 50 may detect the fluid pressure between the syringe 30 and the tubing 45. Similarly, the pressure sensor can be interposed between the syringe tubing 45 and the needle 140. Further still, the in-line sensor may be embedded into the handle 100 or between the tubing 45 and the handle 100. Another alternative is using a thumb-pad force sensor to detect the force driving the plunger 34 to calculate the pressure within the syringe 30. A command signal from the pressure sensor sends data of pressure to the CPU for calculation to determine the exit-pressure. The exit-pressure value is used to control the motor 70 that controls the flow of fluid from the syringe 30.

Handpiece

Referring to FIG. 3, the handpiece 100 includes a hollow housing 110 and an elongated hollow needle 140 projecting forwardly from the housing. A connector 132 is provided for connecting the handpiece with the fluid line 45 of the injection assembly 10. Specifically, the connector 132 provides a fluid-tight seal for connecting the handpiece 100 at the rearward end of the housing to facilitate connection of the handpiece with the fluid in the syringe. The fluid flows to the handpiece and out through the needle 140. As noted above, the in-line pressure sensor or similar element for detecting a characteristic representative of fluid pressure may be embedded within the handpiece 100.

The handpiece 100 may further include an indicator light 215 configured to provide the operator with prompts. The indicator light 115 may be an LED or other light element that provides a warning light or indicator light depending upon the application. The handpiece may further include an audible indicator 120 such as a piezoelectric audio indicator for providing an audible signal, including, but not limited to a buzz, tone or chime.

Additionally, a control button 125 may be provided for the handpiece. The control button 125 may operate as an on/off button. However, the control button may also be operable to enter various control commands. For instance, the control button 125 may be operable to over-ride one or more operations of the drive unit 50 as discussed further below. Finally, the handpiece 100 may also include an output mechanism, such as a display screen 130 for displaying various information, such as the detected fluid pressure.

As described above, the handpiece 100 may include both a visual and an audible indicator 115, 120. It should be understood that the handpiece does not need to include both an audible and a visual indicator; it could include just a single indicator. Further still, although a visual and audible indicator are described, a variety of alternate indicators could be used instead, such as a vibration element that provides regular vibration indicator signals. Additionally, the handpiece 100 need not include any such indicators. Further still, the audible or visual indicators may be located on the drive unit 50 rather than on the handpiece.

As noted above, the handpiece 100 may include a control button. The control button may be utilized when the needle is not being advanced. In such an instance, pressing the button operates to provide a control signal to the drive unit 50 so that a counter-head pressure value will not be subtracted from the calculation of the exit-pressure (since the needle is not being advanced there is zero, or essentially zero, counter-head pressure). It is understood that the button or control on the handpiece 100 may also be activated to correspond with the forward movements in which the counter head-pressure is subtracted from the calculation of the head-pressure therefore providing a means to distinguish between when the needle is being advanced and when it is remaining stationary within the tissues. In this way, actuation of the button 125 during periods of minimal to zero needle insertion promotes accuracy of the exit-pressure values within the tissues during the procedure. In addition to the switch or control button discussed above, the handpiece may include a second button or control element in which backward movements would add an additional head-pressure value to compensate for the backward movement which causes a decrease in exit-pressure values when moving a needle backward through the tissues.

In the foregoing description, the needle is mounted onto a handpiece that may have additional features. However, it should be understood that various elements may be utilized to carry the needle. For instance, the system may be utilized with an embodiment in which the needle is connected to the tubing set. In such embodiments, the operator can control the intensity of the electrical charge by a controller that is operable independently of the handpiece, such as by a controller on the control unit 50.

System Control

The system includes a user operable input mechanism, which allows the operator to provide input signals for controlling the system. The input mechanism may be any of a variety of devices, such as the handpiece 100 or a foot operated control that provides a means for the operator to start, stop, and change the flow-rate from a single flow-rate to a second or third distinct pre-set flow rate. Alternatively, the input element may be a button, touchscreen, mouse, keyboard or a microphone for providing input commands audibly. Additionally, the system may include a plurality of input mechanisms to allow the operator to input a variety of inputs for various stages of a procedure. For example, the system may include a first input mechanism, such as a foot pedal or a remote actuator that controls the flow of fluid through the device. It is anticipated that the remote can be affixed to the ultrasound transducer thus enabling the operator to use a single hand to control the instruments. Actuating the hand remote or foot pedal switch (i.e. depressing the switch) sends a signal to the CPU of the drive unit, which in turn sends a signal to the motor to drive the motor so that fluid flows from the syringe to the needle 140 as long as the instrument is actuated. Alternatively, actuating the hand remote or foot pedal a first time may operate a start signal to start the fluid flow and the fluid may continue to flow until the operator actuates the foot pedal again. In this way, the second actuation operates as a stop signal to discontinue the fluid flow. Additionally, the system may include a second input mechanism, such as a touch screen so that once an electronic simulation is applied to a patient the operator may input an indication of whether or not muscle twitch was detected or whether a sensation is noticed by the patient. Actuating the foot pedal switch (i.e. depressing the switch) may send a signal to the CPU of the drive unit, which in turn sends a signal to the controller of the electronic stimulator to modify the stimuli in intensity, duration, frequency, incremental or decremental current charge utilizing the Automatic Incremental Electric Impulse (AIEI) with specific Baseline Current. These operator control signals can work separately from one another, i.e., effecting either fluid flow or electric stimulation. Further still, the primary or secondary input mechanism may be a control button, such as button 125 on the handpiece. Actuating the control button 125 may send a signal to the CPU to provide a response input during a procedure.

As described above, the system is operable to control the flow of fluid during a procedure. In addition to using an actuator to control On/Off, the system may provide two or more flow rate settings. In particular, the control unit 50 may incorporate a multi-speed pump that provides a variable flow rate. Similarly, the pump may include two or more pre-set flow rates. In the present instance, the control unit 50 includes an electric motor 70 that control the speed at which the control unit displaces the plunger 34 in the syringe 30. The control unit 50 may control the speed of the motor 70 so that the motor is driven at one of multiple pre-set speeds to provide multiple pre-set flow rates. The different flow rates can be used in conjunction with different pressure settings and different electric stimulation settings during different portions of a procedure. For example, the system may be configured with three pre-sets as shown below in the table. The pre-sets may include various characteristics, such as high and low pressure thresholds, high and low stimulation intensities, flow rate and maximum or shut-off pressure. When the measured fluid pressure is above the "Low Pressure" threshold, electric stimulation is provided at the level identified as "Low Pressure Stimulation". When the measured fluid pressure is above the "High Pressure Threshold, electric stimulation is provided at the level identified as "High Pressure Stimulation". The "Flow Rate" is the flow rate of fluid provided from the fluid reservoir (e.g. syringe 30). The "Shut-off Pressure" is the fluid pressure at which the system will interrupt fluid flow. Specifically, if the measure fluid pressure exceeds the shut-off pressure, the control assembly 50 will stop the pump to stop the flow of fluid to the needle.

|  | Low Pressure (mm/Hg) | High Pressure (mm/Hg) | Low Pressure Stimulation (mA) | High Pressure Stimulation (mA) | Flow Rate (mL/sec) | Shut-off Pressure (mm/Hg) |
|---|---|---|---|---|---|---|
| Pre-set 1 | 50 | 200 | 0.4 | 1.0 | 0.02 | 300 |
| Pre-set 2 | 75 | 400 | 0.7 | 1.4 | 0.1 | 500 |
| Pre-set 3 | 100 | 650 | 1.0 | 1.8 | 0.2 | 750 |

As noted above, the different pre-sets may be used during different portions of a procedure. For example, this first pre-set may be used during a first portion of a procedure, such as the portion of the procedure in which the operator is attempting to position the tip of the needle adjacent the target nerve. During this "Locate the Target" portion of the procedure a constant low "Flow Rate" is used to allow for increased sensitivity to the pressure changes. After the needle is positioned adjacent the intended target, the system may switch to a second pre-set. During the second pre-set, the Flow Rate is increased to provide a confirmation of the needle placement. In particular, if the system is used in connection with ultrasound, the location of the needle may be difficult to detect depending on a number of variables, such as the orientation of the needle. However, if a rapid infusion of fluid is provided as defined in pre-set 2, the fluid will appear on the ultrasound display as a dark anechoic pocket of fluid. In this way, the location of the pocket of fluid on the ultrasound image will indicate the location of the needle. Additionally, the particular shape of the fluid on the ultrasound image may provide confirmation that the needle is extra-neural rather than intra-neural. For instance, a donut-shaped fluid space can confirm that the needle is in close proximity to the nerve and extra-neural. Therefore, seeing such a shape may provide confirmation of proper needle placement. It should be understood however, that a variety of shapes can be used as confirmation that the needle is extra-neural.

After the needle position is confirmed using the second or "Confirmation" pre-set, the third pre-set (Pre-set 3), referred to as the "Infusion" pre-set is used. This third pre-set has a higher Flow Rate so that the bolus of medication can be rapidly infused at the target location adjacent the nerve for maximum efficiency.

The switch between pre-sets can be manual or automatic. For example, the operator may manipulate an input device, such as a keyboard, touch pad, a button on the handpiece or otherwise, as noted above. Alternatively, the system may automatically switch to the second pre-set based on detected criteria, such as the fluid pressure, electrical impedance, or change in electrical impedance. The control unit 50 may be preconfigured with different pre-set characteristics, such as the pre-sets described above. For example, the pre-set characteristics can be set by the operator before a procedure or the pre-set values may be pre-programmed into the system. Additionally, the system may allow the user to modify the pre-set characteristics during use. Further still, it should be understood that any number of pre-sets may be utilized. Three pre-sets are described above; however, the system may use fewer pre-sets. For instance, the system may not include any pre-sets and the user may simply change the different values during a procedure. Alternatively, the system may be programmed to include only two pre-sets, such as the "Target Location" pre-set and the "Infusion" pre-set. Further still, the system may include four or more pre-sets that include different operating characteristics for different applications. Incremental mode: triggered during the on-demand procedure or automatic for a defined pressure threshold, the current increases in pre-defined steps over a short duration to detect or not a motor response for instance 0.2 mA is the Target mode 1, in case of rise in pressure the current charge increases step by step relatively quickly to 2 mA; the operator can stop the current in case of motor response.

Method of Operation

An exemplary method for administering a nerve block injection using the system described above will now be described. It should be understood that the present system is not limited to use in peripheral nerve block procedures. Accordingly, it should be understood that the principles and methods described below may be readily adapted for injections into tissues and anatomical areas in a variety of applications and procedures.

The system may be used to detect whether the needle is positioned indenting or within the fascicle (i.e. positioned intra-fascicularly). The system makes the determination based on a combination of several variables. First, if the needle has pierced the perineurium the fluid pressure will be quite high because the axons are tightly packed within the endoneurium and the perineurium defines a boundary of a rigid poorly-compliant component. Additionally, if the needle has pierced the endoneurium the operator is likely to observe a noticeable electric motor response (EMR) to a low current charge electrical stimulation applied to the patient at or adjacent the needle tip. Further still, as the needle approaches the nerve, the nerve may respond to a lower intensity electrical charge (<2 mA). Therefore, various features may be monitored to determine whether the needle is positioned intra-fascicularly and therefore should be re-positioned. Therefore, the system may operate as follows.

Referring to FIG. 4, at step 500 the operator selects the procedural parameters, such as the upper threshold and/or the fluid flow rate and/or the fluid pressure at which electrical stimulation commences, or a baseline current charge to start the procedure. For example, the operator may set an upper threshold pressure, such as 300 mm/Hg and the operator may set a threshold for commencing electrical stimulation or commencing incremental current charge above the baseline current at 50 mm/Hg. Alternatively, the upper threshold may be pre-set in the system when the operator selects the type of procedure for which the system is to be used. Similarly, the operator may select the fluid flow rate through the needle or the flow rate may be set automatically when the operator selects the type of procedure. Additionally, the operator may select characteristics of the electrical nerve stimulation that is to be applied, such as frequency, high intensity, low intensity, baseline current charge, steps of incremental current charge in intensity, duration frequency, interval etc. Once the procedural parameters are selected, the operator provides an indication that the procedure is to start. For instance, the operator may press a start button on the drive unit.

At step 510 the operator advances the needle into the patient. The needle may be advanced at any of a variety of insertion rates, such as 1-3 mm/sec. Preferably, the needle is inserted at a substantially constant rate. Additionally, the control system provides a continuous flow of ionic fluid through the needle tip during the procedure. The flow rate may vary depending on different parameters as discussed previously. For instance, the fluid flow may be infused at approximately 0.02 mL/sec unless the fluid pressure in the needle exceeds a maximum threshold.

At step 520 electric stimulation (ES) is applied. For instance, the electrical stimulation is applied via the needle tip of an insulated needle. The ionic fluid infused through the needle reduces the impedance, which can reduce pain or discomfort that the patient may feel from the electric stimulation. The intensity and frequency of the electric stimulation may vary depending on the parameters established during set-up step 500. Although FIG. 4 shows the electric stimulation as starting once the needle is inserted into the patient, it should be understood that the electric stimulation may not commence until later in the procedure. For instance, the electric stimulation may not commence until the measured fluid pressure exceeds a threshold. In such a method, the electric stimulation would not commence until step 540 as discussed below.

At step 530 as the operator advances the needle, the system continuously determines the fluid pressure at the needle tip and provides feedback either visually or audibly regarding the determined pressure. For example, as described above, the system may include a pressure sensor 40 operable to measure the fluid pressure in-line with the needle. The sensor may provide signals to the control unit 50 that may be used to control the electric stimulation.

At step 535 the system compares the detected fluid pressure with a pre-determined threshold. In the present instance, step 535 occurs during infusion of the drug. If the detected fluid pressure does not exceed the threshold then the method returns to step 510 and the operator continues to advance the needle to attempt to locate the target nerve. If the system detects that the fluid pressure exceeds the threshold then the method proceeds to step 540.

At step 540 the pressure exceeds a threshold so a characteristic of the electrical nerve stimulation is varied. For instance, as noted above, the electrical stimulation may not commence until the fluid pressure exceeds a first threshold. If the fluid pressure exceeds the first threshold then the system commences electrical stimulation at step 540. Similarly, if the fluid pressure exceeds a second threshold then the system varies the intensity of the electrical stimulation at step 540 and continues to apply electrical stimulation. For instance, the system may be configured so that the electrical stimulation is applied at 1.0 mA when the electrical stimulation commences. If the fluid pressure exceeds a second threshold then the intensity of the electrical stimulation may be reduced, such as by lowering the electrical stimulation to 0.4 mA.

At step 540 the electric nerve stimulation may be varied manually or automatically by the system in response to the fluid pressure exceeding the upper threshold. For instance, once the fluid pressure exceeds the second threshold the system may automatically vary the electrical stimulation (such as by commencing or by varying the intensity). Alternatively, the system may provide a signal to the user (such as an audible or visual signal) and the operator may vary the electric stimuli by manipulating a control element such as a button or touchscreen. In response to the operator's prompt, the electric nerve stimulation is varied and applied to the patient.

At step 545 the patient is monitored to detect any clinically observable response, such as a muscle twitch. As discussed below, this monitoring may be manually, such as by the operator visually observing the muscle twitch and then actuating a input mechanism, such as a push button. Alternatively, the monitoring may be automatic. Specifically, the system may include a sensor for detecting the twitch. If the sensor detects a characteristic indicative of a muscle twitch, then the sensor provides a signal to the system indicating that a twitch was detected. If a twitch is not detected in response to the electric stimulation then the method returns to step 510 and the operator continues to advance the needle. If a twitch is detected then the needle may be adjacent the target nerve. However, since the fluid pressure exceeds the second threshold, the needle may be intra-fascicular, which could lead to damage or complications if the anesthetic is injected while the needle is in the nerve. Accordingly, if a twitch is detected at step 545 the method may proceed to step 550.

At step 550 the operator repositions the needle in an attempt to position the needle tip adjacent the nerve but not in the nerve or in direct contact with the surface of the perineurium of the nerve. For instance, the operator may withdraw the needle slightly and then attempt to position the needle tip adjacent the nerve. The step of repositioning may be guided by ultrasound so that the operator may be able to visually confirm that the needle is withdrawn from the nerve and then repositioned adjacent the nerve. If the needle was positioned within the nerve, the fluid pressure would exceed the second threshold as described above. As in example Pre-set 1, if the pressure exceeds the pressure threshold value 300 mm/Hg and the operator detected a muscle twitch from a reduction in the electrical stimulation intensity then the operator sends an input signal and the system will provide a warning or alarm and prevent further infusion of fluid by the operator. If the needle is then withdrawn, then the fluid pressure should fall below the threshold so fluid flow can re-commence. Accordingly, after re-positioning the needle the method moves on to step 555.

At step 555 the fluid pressure is evaluated to determine whether the fluid pressure exceeds the second threshold. If the fluid pressure exceeds the second threshold, as by this example 300 mm/Hg (Pre-set 1), then the needle tip may still be within the nerve. Accordingly, the method returns to step 550 so that the needle may be re-positioned. Alternatively, the needle may be withdrawn and the process may re-start at step 510. If the step of re-positioning the needle has withdrawn the needle tip from being within the nerve (i.e. intra-fascicular), then the withdrawal of the needle will cause the fluid pressure to drop below the second threshold. Therefore, if the fluid pressure drops below the second threshold then the method proceeds to step 565.

At step 565 the electrical stimulation is applied and the operator observes whether a twitch is observed in response to the electrical stimulation. If the operator observes a twitch, the operator may then provide an input to the system indicative of whether an observable response was detected or not. For instance, the operator may press a first button if the operator noticed a twitch or the operator may press a second button if the operator did not notice a twitch. It should be noted that the electrical stimulation that is applied is the electrical stimulation that was varied at step 540. For example, if the fluid pressure exceeded the second threshold and the intensity of the electrical stimulation was decreased, then the electrical stimulation will continue to be applied through step 565. Therefore, if the operator observes a twitch at step 565 the operator has confirmed that the nerve has responded to the varied (i.e. increased or decreased intensity) electrical stimulation and that the fluid pressure is consistent with being extra-neural. Accordingly, if the operator observes a twitch in response to the electrical stimulation then the method proceeds to step 570. If the operator does not observe a twitch then the procedure returns to step 510 to re-start the search for the target nerve.

At step 570 the system provides a signal to the operator indicating that the needle is properly located for an injection (i.e. the needle tip is located extra-fascicularly). For example, the control unit 50 may provide an audible signal such as announcing the word "proceed" or providing a visual signal, such as the word "proceed" on the display screen of the drive unit or the handpiece.

Figure 5:
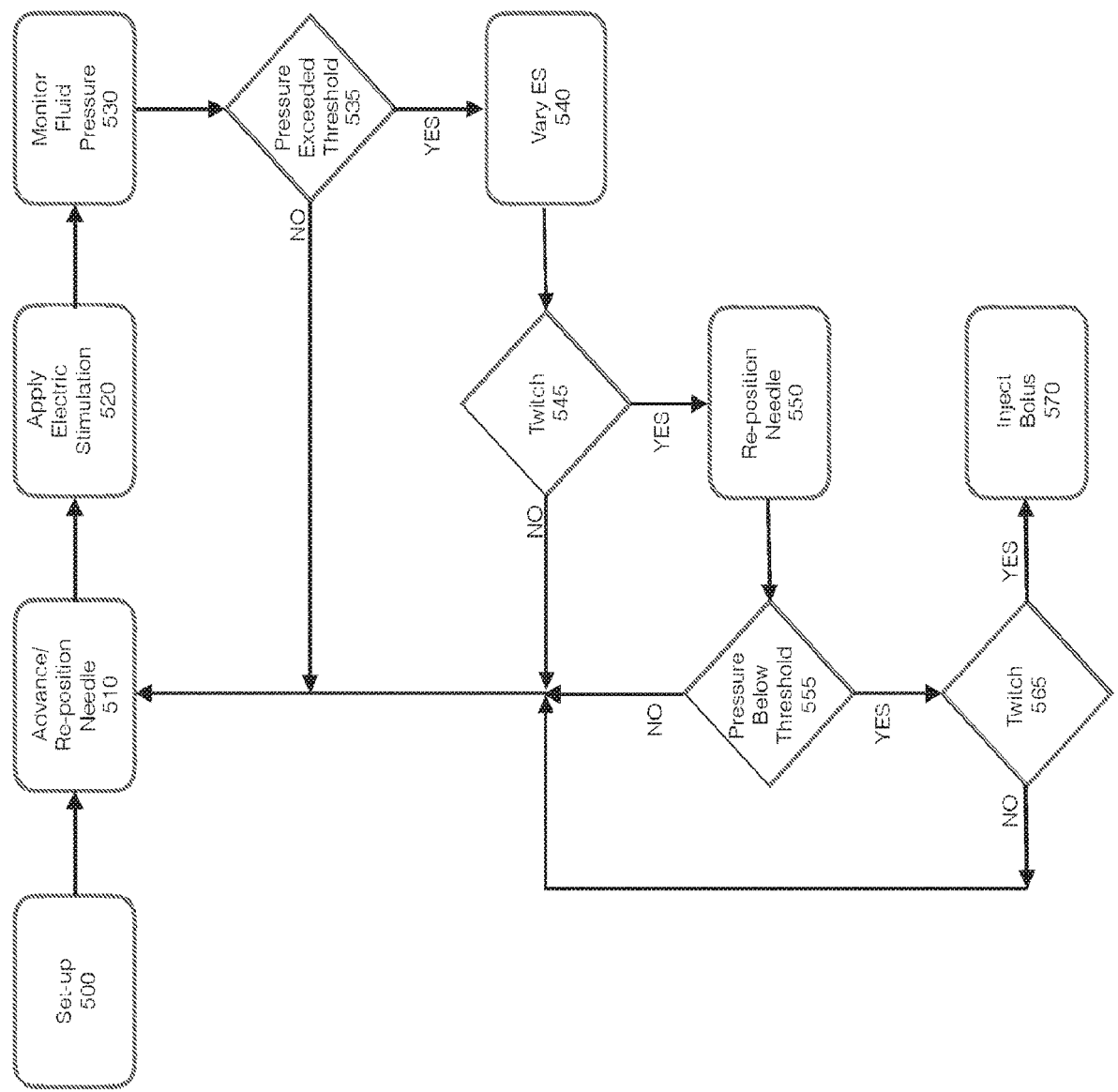
FIG. 5 is a flow chart of a method for injecting fluid.

At step 570 the flow rate of fluid is increased to a second rate that is higher than the first rate. The operator may inject a preliminary amount that may be observable so that the operator may detect that the needle is properly placed. Once placement is verified, the operator may inject a bolus of fluid to anesthetize the patient. Alternatively, the operator may inject the bolus of fluid without first injecting an amount to verify the needle placement. Either way, a quantity of fluid is injected at step 570 at a higher rate than the previous low flow rate. For instance, the drive unit may automatically increase the flow rate, such as by increasing the speed of the motor As discussed above, the system may combine various measured characteristics to assess whether the needle is positioned adjacent the target nerve and whether the needle is intra-fascicular or extra-fascicular. In the exemplary method illustrated in FIG. 5, the method incorporates features regarding the fluid pressure at the needle tip as well as the intensity of the applied electrical stimulation.

It should be understood that the values provided above, such as the threshold of 300 mm/Hg as the maximum pre-set pressure for stoppage of fluid flow is an example and that either a lower or higher pre-set pressure may be selected at the discretion of the clinician. Similarly, the values of 0.4 mA and 1.0 mA for the lower and upper electrical intensities are examples and either higher or lower values may be set. However, in the present instance, it may be desirable to select an upper amperage that does not exceed 2.0 mA. The techniques described herein are equally applicable to human and animal tissues.

Variable Incremental Electrical Current Charge

In the foregoing description, the system is described as providing an electrical impulse or charge that may vary in response to certain characteristics, such as a fluid pressure being detected above a threshold. However, prior to the detection of the characteristic, the electrical impulse was generally fixed. However, it may be desirable to provide an electrical impulse that is continuously variable, as discussed further below.

Figure 6:
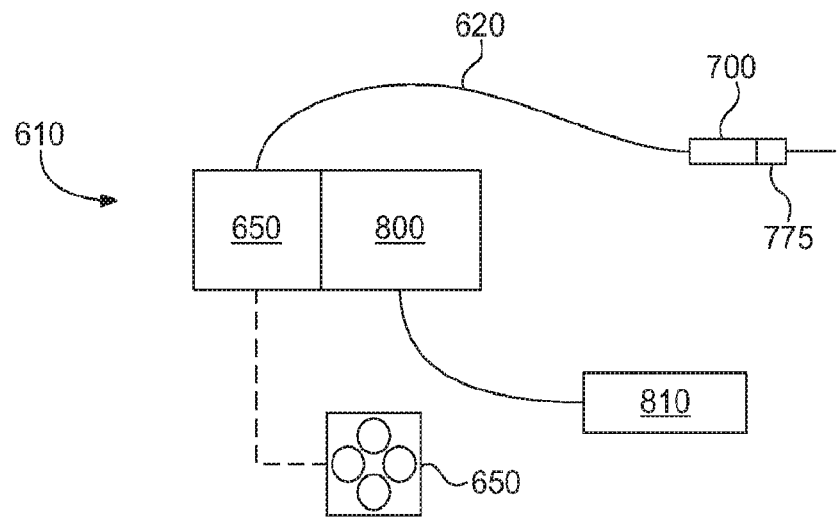
FIG. 6 is a diagrammatic view of an alternate embodiment of a drug delivery system.
Figure 7:
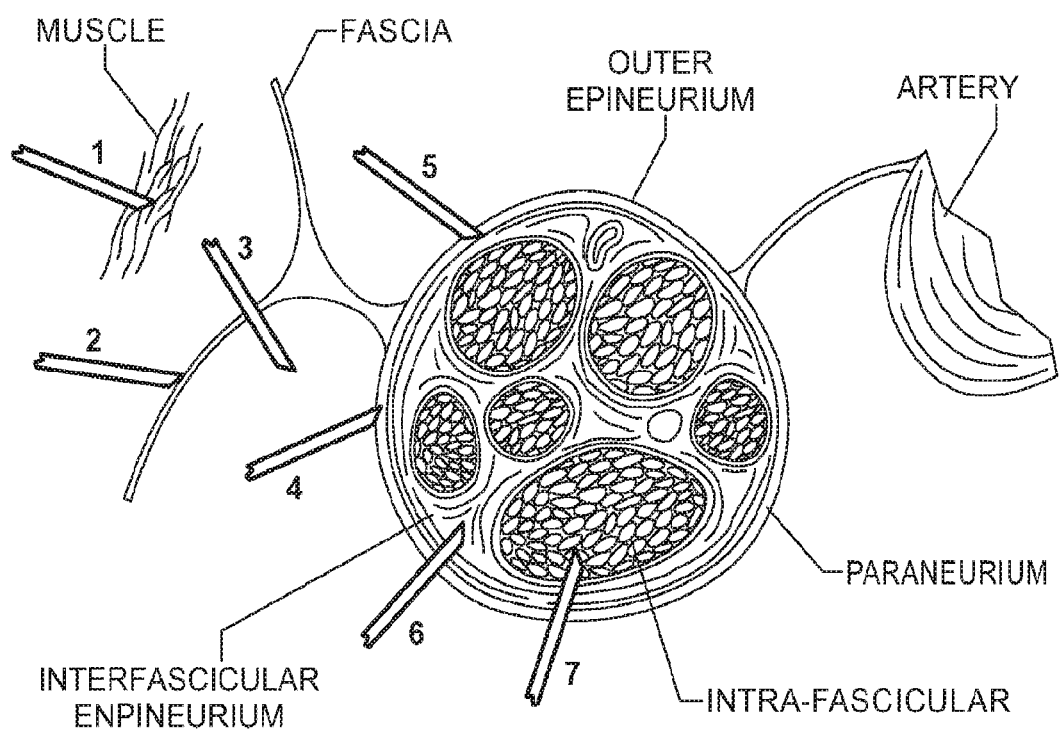
FIG. 7 is a diagrammatic view of a target nerve.
Figure 8:
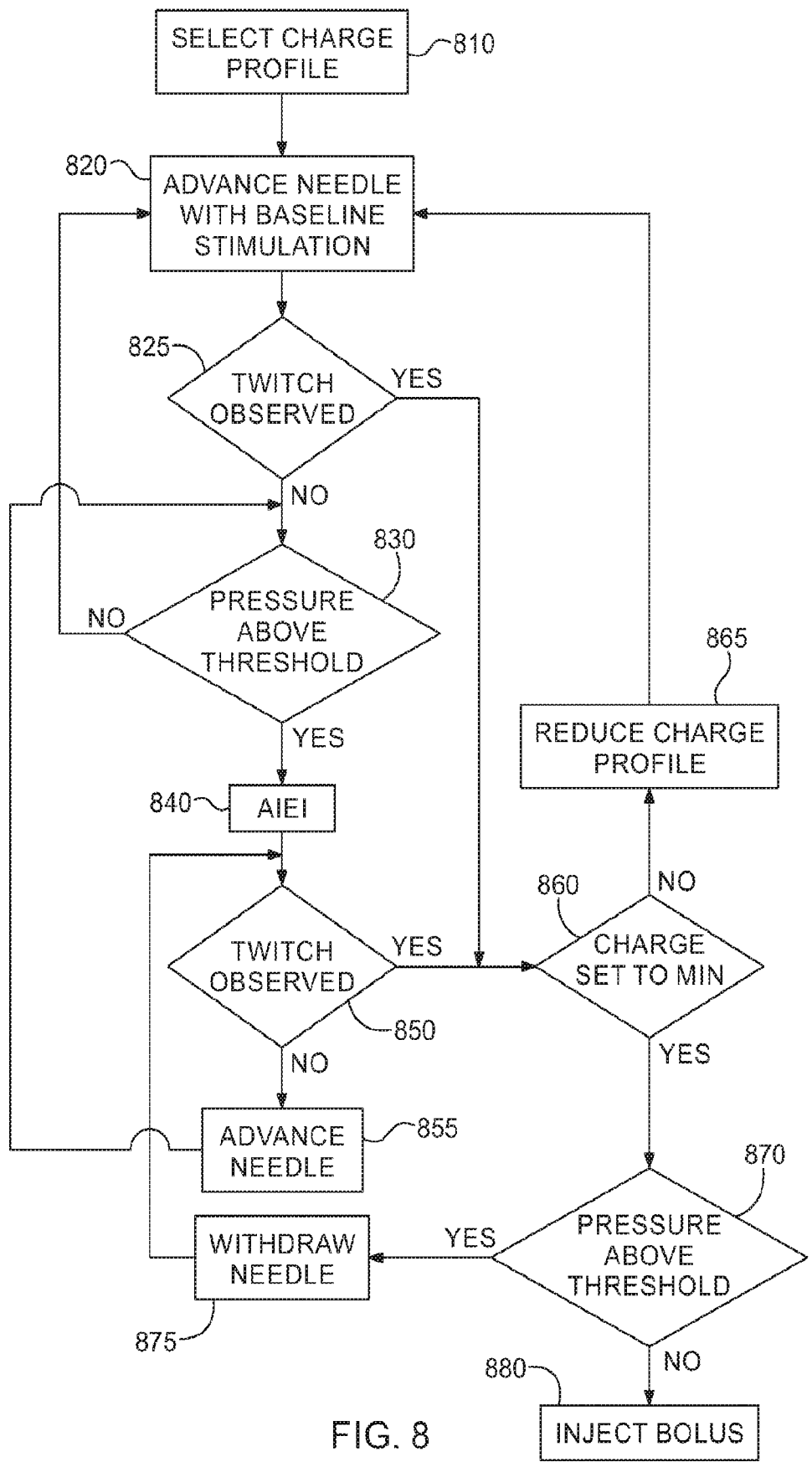
FIG. 8 is a flow chart of an alternate method for injecting fluid.

Referring now to FIGS. 6-8 an alternate embodiment of the system is illustrated. The system 610 is configured similar to the system 10 described above, except that the system includes a separate actuator and the system includes a controller programmed to provide electrical stimulation in which the electric impulse continuously varies.

The system 610 includes a drug delivery system 650 configured similarly to the system 10 and drug delivery system 50 described above. Similarly, the system 610 includes an injection assembly 620 and a handpiece or needle assembly 700. Except as otherwise described below, elements 620, 650 and 700 are configured similar to the corresponding elements 20, 50 and 100 described above.

The system 610 further includes a remote actuator 750. The remote actuator 750 may be a separate element or it may be incorporated into the handpiece 700. Alternatively, the handpiece 700 may be a simple handle and the remote actuator 750 may separate. Further still, the remote actuator 750 may actually be incorporated into the drug delivery system 650. Regardless of whether the remote actuator is a separate element or incorporated into another element of the system, in the following description, the actuator is referred to as a remote actuator.

In the present instance, the remote actuator 750 is a separate manually actuable element that is connected with the drug delivery system 650. The remote actuator may be any of a variety of actuators, such as a handheld device with one or more input mechanisms, such as buttons or the like. Alternatively, the remote actuator may incorporate a single actuator that controls the operation of the system by the manner in which the actuator is operated. For instance, the remote actuator may be a foot pedal so that the operator may operate the actuator without using one of his or her hands. The operator may send different commands to the system by varying the manner in which the foot pedal is operated. For example, a single click (press and release) of the foot pedal may send a first command signal to the drive unit 650 whereas a quick double click may send a second signal to the drive unit. Further still, the remote actuator may comprise a voice actuated element so that the operator can provide control signals to the drive unit by voice actuation.

As mentioned above, the control unit 650 may be configured to control a variety of operational controls in response to signals received from the remote actuator 750. For instance, the remote actuator may be operable to control one or more of the following parameters:

Flow rate: Fluid flow from the drive unit 650 may be manually changed by actuating the remote actuator (e.g. pressing a button). Each time the actuator is actuated the control unit may increase the flow rate in predetermined increments (e.g. 0.02 ml/sec). Alternatively, the flow rate may be varied by pressing and holding the actuator to increase the flow rate until the actuator is released (similarly, the flow rate may be reduced in incremental steps).

Rapid flow: actuating the remote actuator may provide a burst of fluid (e.g. 0.1 ml/sec) to verify the appropriate location of the needle tip at the beginning of Local anesthetic injection Turbo flow: actuating the remote actuator may inject a bolus of anesthetic when the needle is properly placed (e.g. 0.2 ml/sec).

Aspiration cycle: the syringe plunger of the drive unit 650 is reversed by actuating the remote actuator. Reversing the plunger is operable to aspirate the syringe to determine whether the needle tip has entered a blood vessel and to identify blood in the needle hub or tubing during aspiration.

"Stop": actuating the remote actuator stops the flow of fluid from the drive unit 650.

AIEI Actuation: the electric stimulation can be controlled by the remote actuator, such that actuating the remote actuator starts or stops AIEI.

Nerve Stimulator: a characteristic of the electric impulses provided by the stimuli generator may be controlled by the remote actuator. For instance, the intensity of the electric impulses may be varied or discontinued. Similarly, the Charge Profile described below can be changed by actuating the remote actuator.

The remote actuator may interface with the control unit 650 using a wired or wireless connection. For instance, the remote actuator may be a handheld remote with multiple control buttons that interfaces wireless with the control unit 650 by Bluetooth or a similar wireless convention. Regardless of the structure of the remote actuator, the remote actuator is configured to be actuated by the operator during the procedure to send one or more control signals to the drive unit to control the fluid flow or electrical stimulation provided by the system.

As described further below, the system 610 may be configured to provide a continuously variable electrical impulse. This variable electric impulse is referred to herein as Automatic Incremental Electric Impulse (AIEI) current stimulation. This term AIEI can be understood as defined as a Charge Profile consisting of a set of pre-defined pre-set charge values for nerve stimulation. The AIEI may be used instead of a constant stimulation or the AIEI may be used in combination with a constant stimulation. For example, as discussed further below, the system may use a constant electric impulse during a portion of a procedure and during another portion of the procedure the system may provide AIEI stimulation. Accordingly, the system 610 may be configured to include several different modes of operation so that the operator may select from the several different modes depending upon the operator's preference or the characteristics of the procedure. For instance, the system 610 may be programmed to include a Manual Mode, an Automatic Mode, a Semi-Automatic Mode, as follows:

Manual mode: the nerve stimulator can be controlled by the operator via the remote actuator 750. The operator can control the flow-rate of the fluid from the drive unit 650 and nerve stimulation as separate manually controlled parameters.

Automatic mode: pressure controls initiation of AIEI. In addition, when a minimal intensity charge is combined with a defined maximum pressure threshold in which a EMR (electrical motor response) is identified the system discontinues fluid flow to the needle. These conditions may also be combined with an alert or warning to the operator that such conditions have been met and serves as an "alert" condition and "red-flag" condition not to proceed with injecting fluid into the patient.

Semi-automatic mode: pressure sensing can be operated in conjunction with a single pulse electrical charge in which the conditions of pressure threshold and minimal intensity charge elicit EMR the system automatically alerts and stops the flow of fluid based on the response and observational input of the electric motor response to the system.

As described above, the control unit 650 includes a stimuli generator for providing electrical impulse for nerve stimulation. The stimuli generator may be programmed to provide a variety of different profiles for the electrical impulses, including, but not limited to the following:

No Nerve Stimulation Mode: no electrical current is emitted.

Single Pulse Mode: the system emits a single pulse having a particular intensity and duration (current charge)

known as a single pulse or twitch. For example, a pulse of 0.1 to 6 mA at 0.1 ms or 0.5 to 6 mA-1 ms, 1 to 4 Hz.

AIEI Mode: a series of varying electrical impulses is provided. The impulses may start with a first electric impulse and increase incrementally in stepwise fashion to a maximum value and then re-set to the minimum value. In this way, the stimuli generator provides a series of impulses that continuously vary in stepwise fashion as long as the AIEI is active.

The goal of the nerve stimulation is to produce a noticeable muscle twitch or EMR as described above. The operator may monitor the patient to detect an EMR. In response to the EMR, the operator may input data into the system indicative of an EMR being observed in response to the nerve stimulation. For instance, the operator may operate an actuator, such as remote actuator 750 if the operator observes an EMR. Alternatively, the system may include a sensor 775 for detecting a characteristic indicative of an EMR. The sensor may be a separate element or it may be included in the handpiece on which the needle is mounted. For instance, the sensor 775 may include an electrode accelerometer or electromyograph sensor or similar element to detect vibrations indicative of a muscle twitch in response to the nerve stimulation. In response to detecting the characteristic indicative of a twitch, the sensor 775 provides a signal to the drive unit indicative of a twitch occurring. As described further below, the system may control further operation of the fluid and the nerve stimulation in response to the signal indicative of a twitch occurring.

In the foregoing description, the system incorporates a drug delivery system 650 that incorporates a stimuli generator for providing a series of electric impulses to provide nerve stimulation for determining whether the needle is in an appropriate location relative to a nerve. It may also be desirable to incorporate an ultrasound probe for providing some visual guidance to the operator. In particular, the system may include an ultrasound system 800 that includes a probe 810 that includes an ultrasound transducer for emitting and receiving sound waves and communicating signal regarding the sound waves to an ultrasound processor to produce sonogram images. The system 610 may also include a display for displaying the ultrasound images to display images of the needle relative to the target nerve. Additionally, it may be desirable to incorporate the remote actuator 750 into the ultrasound elements. For instance, the remote actuator 750 may be incorporated into the ultrasound probe 810 so that the fluid flow and/or nerve stimulation can be controlled remote by the actuator on the ultrasound probe.

With the foregoing in mind, the system may be used to provide a series of electrical impulses to provide nerve stimulation and the characteristics of the electrical impulses may vary during different portions of a procedure. Additionally, the characteristics of the electrical impulses may vary based on whether supplemental information provided by the system indicates the proximity of the needle tip to the target location. For instance, if ultrasound is used and the images provide clear images of the needle relative to the target nerve, then the ultrasound provides information that guides the needle into proximity of the nerve. In such instances, the operator only needs to use the nerve stimulation to guide then needle during the last portion of the needle insertion. In other words, during this localized mode, the nerve stimulation is used to guide the needle once the needle is already in relative proximity to the target nerve. This localized search is referred to as a Target Mode. In contrast, if the operator does not have supplemental information regarding the location of the needle, then the nerve stimulation is used to guide the needle to the target nerve from a greater distance. For instance, the images from the ultrasound may not provide a clear indication of the needle proximity to the nerve or ultrasound may not be provided at all during the procedure. In such instances, the nerve stimulation is used to guide the needle from farther away than in the Target Mode. This wide area search is referred to as Search Mode. The system may be configured to provide guidance during both the Search Mode and the Target Mode. Additionally, the system may switch from Search Mode to Target Mode during a procedure. During Search Mode the electrical impulses generally have greater intensity since the needle is farther from the target nerve. During Target Mode, the electrical impulses generally have lower intensity since the needle is closer to the target nerve.

In addition to proximity to the nerve, characteristics of the patient may affect the appropriate electrical impulses. For instance, in pediatric use, generally the electrical impulses are lower than when the patient is an adult. Accordingly, the characteristics of the electrical impulses may be varied based on physical characteristics of the patient.

The system may include a series of pre-defined stimulation profiles based on a variety of variables. For instance, the profiles may be based on whether the system is operating in Target Mode or in Search Mode. Similarly, the details of the profiles may be based on whether the patient is a child or an adult. Accordingly, the system is programmed to include a series of predefined profiles, referred to as charge profiles. Each charge profile includes information regarding the electrical impulses that are to be provided during when the profile is used. For instance, a profile may include the starting or minimum intensity for the current charge. If the profile is for a procedure in which the electrical stimulation varies, such as AIEI, the profile may also include information, such as the maximum intensity for a charge. Additionally, the profile may include the intermediate values between the minimum and maximum and the time between increments. The charge profile may also include the duration of each electrical impulse. Further still, one or more of the charge profiles may include both steady or constant stimulation during a portion of the procedure and variable stimulation during a portion of the procedure. The charge profile may store data regarding the electrical impulses to be provided during both portion of the procedure. The charge profile may also include data regarding the characteristics dictating whether constant or variable stimulation is provided. For instance, the nerve stimulation may start at a constant level in which the stimuli generator provides a series of electrical pulses of constant intensity. If the system detects a fluid pressure at the needle tip above a threshold value, then the system may automatically switch to provide variable stimulation in which the stimuli generator provides a series of electrical pulses of varying intensity.

Referring now to FIG. 7, a diagram illustrates a series of needle tip positions relative to a target nerve designated N. The needle positions are designated 1-7. In position 1 the needle is positioned in muscle, which is distant from the target nerve N. At position 1, the fluid pressure in the needle is relatively low because the muscle is lower density and since the needle is distant from the target nerve, there is no EMR even in response to a high intensity electrical stimulation. In position 2, the needle is in or on fascia, which is a relatively high density structure. Therefore, the fluid pressure will be relatively high; however, since the needle is remote from the target nerve, there is likely no EMR. In needle position 3, the needle is in interstitial material, which is low density, so the detected fluid pressure will be low and no EMR is expected unless the electrical stimulation is high intensity. At position 4, the needle tip is at the paraneurium, so that the needle tip is outside the target nerve but adjacent the nerve. At this point, the detected fluid pressure should be relatively low and an EMR should be observed for both low and high intensity electrical stimulation. At positions 5, 6 and 7, the needle is either within the nerve or within the epineurium or perineurium of the nerve. Therefore, in each of these positions an injection of fluid could damage to the nerve. At each of positions 5-7, an EMR should be observed in response to both high intensity and low intensity nerve stimulation. In positions 5 and 7 the fluid pressure is relatively high, while the fluid pressure at position 6 may be relatively low.

An objective of the system is to guide the needle to needle position 4. In particular, the system enables a PNB injection to be performed in which the location of a needle tip in relation to anatomic structures can be determined by understanding a set of condition when using exit-pressure and electrical motor responses from nerve stimulations in combination to observation or detection of a muscle excitation response or lack of as information to acted upon, either by direct or indirect input into the system or by taking specific action from the muscle response. Thus, pressure and electrical change from the system may be used in combination with an observed or recorded electrical motor response thus enabling one to determine whether the needle is located far from the nerve (e.g. needle positions 1-4), close to the nerve (e.g. needle position 4), on or in the nerve or within the fascicle (e.g. needle positions 5-7). A peak pressure indicates that the needle is located in a dense connective tissue such as a fascia, indenting a nerve or intra-neural, ie., into the nerve itself, intra-fascicular.

Referring now to FIG. 8, the details of an exemplary method using the system 650 will be described.

Step 810: The system includes a plurality of stored data sets regarding the charge profiles that can be used during a procedure. The operator inputs information that controls the operation of the system during the procedure, such as the starting flow rate, the target fluid pressure threshold and the charge profile to be used. The charge profiles programmed into the system may include data for controlling the baseline charge intensity and the Automatic Incremental Electric Impulse (AIEI) current stimulation. Although the system may include a variety of charge profiles, the current example includes four profiles.

Automatic increase of current charge in a short duration 1, 2, 4, 8 hertz location of the nerve. Target Mode 2 and Search Mode 2 are for a second type of patient, such as a pediatric patient. More specifically:

Target Mode1: under ultrasound guidance in good situation (high quality imaging, good echogenicity), the current baseline may be set to the lowest (0.2 mA-0.1 ms) to detect the needle tip is deeper than expected on the ultrasound image (overshoot) causing inadvertent nerve contact or nerve puncture.

Target Mode 2: the baseline current may be set to a higher current for example in case of difficult situation (low quality imaging, poor echogenicity). Utilizing a higher baseline current enables the operator to be informed of the needle tip to nerve proximity at a greater distance than actual intended target when the image is not well defined.

Searching mode 1: for example, under ultrasound guidance to differentiate a tendon from a nerve. Approaching the structure a motor response will be observed in front of a nerve no motor response will be observed in close proximity to the tendon. In this mode, a greater current charge is employed to assist the operator to identify and initial EMR to assist in guidance toward the intended final target.

Searching mode 2: for example, without ultrasound, to detect a nerve structure at a distance from the needle tip. This mode is used to when at greater distance from the intended target by the operator. It provides the operator guidance by emitting a higher electrical charge (starting at 0.5 mA-1 millisecond) which may elicit a motor response at a greater distance from the intended target.

As noted above, an ultrasound display may provide some visual guidance during the process, but other than selection of the charge profile, the method below is described without input from the ultrasound.

During this step, the system is initiated by starting the system via the input mechanism on the drive unit 650 or the remote actuator 750. The system is set up using a Syringe (e.g. 20 mL), with a nerve stimulating needle 22-Gauge (19-G to 25G length 25 mm to 15 cm). Tubing is provided as a high durometer, reduced diameter currently in use the CompuFlo® instrument. This will activate the drive unit 650, which initiates the flow-rate. In the present instance, the initial flow rate is 0.01 mL/sec. and the initial nerve stimulation is a constant value, referred to as the Baseline electrical current. Step 820: After the charge profile is selected, the operator advances the needle while the system provides a continuous minimal flow of fluid and the stimulator provides the Baseline current charge.

TABLE A

| Mode Current | Baseline current | AIEI | | | | | | | |
|---|---|---|---|---|---|---|---|---|---|
| | | Min | Step 1 | Step 2 | Step 3 | Step 4 | Step 5 | Step 6 | Max |
| Target mode 1 | 0.2 mA | 0.3 | 0.4 | 0.5 | 0.7 | 1 | 1.5 | 2 | 2.5 |
| Target mode 2 | 0.5 mA | 0.7 | 1 | 1.5 | 2 | 2.5 | 3 | 4 | 5 |
| Search mode 1 | 1.0 mA | 1.5 | 2 | 2.5 | 3 | 4 | 5 | 6 | |
| Search mode 2 | 0.5 mA | 1 | 2 | 3 | 4 | 5 | | | |

Target Mode 1 and Search Mode 1 are charge profiles for a first type of patient, such as for an adult patient. Search Mode 1 is a high intensity profile or "search" profile used during a wide area mode, such as when the ultrasound image is low quality. Target Mode 1 is a minimum intensity profile or "target" profile, when the needle is likely to be in the Step 825: If a muscle twitch is observed, then the needle may be in the area of the nerve. Therefore, as the operator advances the needle, the operator observes the patient to identify whether the Baseline stimulation cause a twitch. If a twitch is observed, the Method proceeds to step 860 described below. If the operator observes the twitch, the operator may actuate an actuator (such as via the remote actuator 650) to provide a signal to the system indicating that a twitch was observed. Alternatively, the system may include a detector for automatically detecting whether a twitch occurred. For instance, the system by include a sensor for detecting vibrations indicative of a twitch. In response to detecting a twitch the sensor may send a signal to the system so that the system with advance to step 860.

Step 830: While the operator advances the needle, the drive unit 650 constantly measures the fluid pressure of the fluid in the needle. As long as the fluid pressure remains below a threshold, the operator advances the needle and the stimulator provides the Baseline charge. If the fluid pressure exceeds the threshold, then the needle may be on or in the nerve. Therefore, if the fluid pressure exceeds the threshold, the system discontinues the baseline stimulation and switches to AIEI stimulation according to the charge profile being used (this may be the charge profile selected at step 810 or it may be a different charge profile as discussed below at Step 865).

Fluid pressure threshold may be an absolute value (e.g. greater than 200 mm/Hg) or a relative change in pressure exceeding a threshold (e.g. a change in pressure of 80 mm/Hg). It is understood that depending on the anatomic location this pressure threshold could be different; however, typically, the change in pressure is within the range between 50 mm/Hg to 150 mm/Hg.

Step 840: The system initiates AIEI if the fluid pressure exceeds the threshold. During AIEI, the system continuously varies the charge intensity from a lower intensity to an upper intensity. The upper and lower charge intensities are set by the charge profile. Additionally, the intermediate values and the number of intermediate values may be set by the charge profile. For example, in the Target Mode 1 in Table A, the Charge Profile shows the minimum or starting charge intensity for AIEI as well as the six steps between the minimum and the maximum intensity. After the system provides the maximum intensity charge, the next charge is the minimum value. In this way, the system provides a series of charges varying in step wise fashion from the minimum to that maximum. More specifically, once the pressure sensor detects a fluid pressure exceeding the preset threshold (e.g. 80 mm/Hg, the pressure rise would automatically initiate the switch from the Baseline current to AIEI with an incremental increasing charge of 0.3 mA, to 0.4 mA, to 0.5 mA to 0.7 mA to 1.0 mA to 1.5 mA to 2.0 mA to ending with 2.5 mA.

Step 850: Similar to step 825, it is determined whether the AIEI stimulation causes a motor response or muscle twitch. This can be determined manually by the operator observing the twitch or automatically if the system includes a sensor for detecting the twitch.

Step 855: If no twitch is detected, the operator continues to advance the needle while the system provides AIEI stimulation and the operator and/or the system continues to monitor for twitch. The AIEI stimulation may automatically restart until the pressures remains high and may stop when the pressure drops below the pressure threshold going back to Step 820.

Step 860: If twitch is observed, then the system determines whether the charge or charge profile is set to the minimum charge profile. For instance, the system may detect whether the charge profile is set to a "Search" profile, such as Search 1 or if the charge profile is set to "Target" profile, such as Target 1.

Step 865: If the charge profile is NOT set to the minimum, then the charge profile is reduced to the next lowest charge profile. In the example described above, the charge profile would be reduced from Search 1 to Target 1. This change may be made automatically in response to the input regarding the muscle twitch being detected or the operator may manually make the change once the muscle twitch is observed and the operator sees that the charge profile is not set to the minimum charge profile.

Step 870: If the charge profile is set to the minimum and a twitch is observed, then the needle may be in or near the nerve. If the needle is in the nerve, then the bolus of fluid should not be injected. If the needle is in the nerve, the fluid pressure will be high. Therefore, before allowing the bolus of fluid to be injected, the system determines whether the fluid pressure is above a threshold.

Step 875: If the fluid pressure is above the threshold then the needle may be within the nerve. Accordingly, the needle should be withdrawn. If the needle is within the nerve, then withdrawing the needle slightly should position the needle at the appropriate location. Therefore, after the needle is withdrawn, the method may return to step 850 in which AIEI is provided and the system/operator monitors for a muscle twitch. However, in some instances, safety will dictate that the needle should be withdrawn further, so that the method returns to step 820.

Step 880: If the fluid pressure is below the threshold and a muscle twitch is observed at the low charge intensity, which is indicative of the needle being near the nerve and the low fluid pressure is indicative of the needle being outside the nerve. Therefore, the bolus of medicine can be injected.

As described above, the method is operable to guide a needle to the target nerve. In particular, the method is able to provide a safety mechanism for ensuring that an injection is not provided while the needle is intra-neural. For instance, if the system detects a signal indicative of the fluid pressure exceeding a threshold and a signal indicative of an EMR in response to minimal intensity electrical stimulation, then the system will provide an alert, warning or alarm and prevent further infusion, which is indicative of the needle within the nerve. As noted previously, the signal regarding the EMR may be provided manually by the operator or the system may include a detector that provides the signal automatically in response to the EMR. Additionally, the system may be configured to control the flow of fluid so that fluid flow to the needle is discontinued in response to signals indicative of high fluid pressure and EMR caused by minimum nerve stimulation.

In the foregoing description, the system 610 is used to identify whether the needle is within a nerve and to therefore provide an indication to the operator if the needle is within the nerve. Additionally, the system may control the fluid flow in response to determining that the needle is within the nerve. Specifically, the system may prevent the flow of fluid if the it is determined that the needle tip is within the nerve. The system makes determination of the needle location in response to a plurality of criteria. In particular, a fluid pressure exceeding a threshold and a detectable muscle twitch in response to a minimum electric stimulation. In addition to detecting whether the needle tip is within a nerve, as discussed further below, the system may be programmed to detect whether the needle tip is positioned within a dense tissue that is not a nerve.

As noted above, the system 610 may include a plurality of presets and/or programs. The operator may initiate a procedure for identifying a dense tissue that is not a nerve by selecting a stored profile corresponding to such a procedure. As with step 820 of the above method, the operator will advance the needle using a Baseline stimulation. If a muscle twitch is detected, then the needle may be adjacent a nerve. Therefore, in response to detecting muscle twitch, the needle is re-positioned. If the fluid pressure exceeds a threshold, then the needle is likely in a dense tissue. As with step 840, if the fluid pressure exceeds the threshold AIEI is started. Again, if muscle twitch is observed, the needle is re-positioned. In contrast, if the fluid pressure remains above the fluid pressure threshold and no muscle twitch is detected in response to the elevated electrical stimulation, then the system may provide a signal indicating that the needle is positioned with a dense tissue that is not a nerve. Additionally, in step 840 AIEI is provided. However, in this mode in which the operator is attempting to locate a dense tissue that is not a nerve, the charge profile may be raised to a continuous maximum value designed to ensure that the needle is not adjacent a nerve.

In this way, the system receives criteria regarding the fluid pressure, the level of electrical stimulation and whether or not the electrical stimulation caused and EMR. Based on these criteria, the system is configured to determine whether the needle tip is positioned in or on a dense tissue that is not a nerve. Additionally, the system may be configured to control the flow of fluid so that an injection can only be provided if the three criteria are met: fluid pressure above a threshold, electrical stimulation above a threshold and no detection of a muscle twitch.

It will be recognized by those skilled in the art that changes or modifications may be made to the above-described embodiments without departing from the broad inventive concepts of the invention. For instance, in the foregoing description, the system is described in the context of providing fluid infusion. However, it should be understood that the system may be used for placement of a needle to aspirate fluid-filled tissue. It should therefore be understood that this invention is not limited to the particular embodiments described herein, but is intended to include all changes and modifications that are within the scope and spirit of the invention as set forth in the claims.

What is claimed is:

1. A system for providing a peripheral nerve block to a patient, comprising:
   a needle having a sharpened tip;
   a fluid pump providing a flow of fluid to the needle,
   a controller for controlling the fluid pump to control the flow of fluid to the needle;
   a sensor for detecting a fluid pressure in the needle; and
   a conductive element for providing an electric nerve stimulation at the tip of the needle;
   wherein the controller is disposed in communication with the conductive element, and is configured to provide varying electrical stimulation through the conductive element in response to the sensor detecting a fluid pressure above a first threshold, and
   wherein the controller is configured to discontinue the flow of fluid to the needle in response to the sensor detecting a fluid pressure above a second threshold and an indication of an evoked muscle response from the electric nerve stimulation.

2. A system for providing a peripheral nerve block to a patient, comprising:
   a needle having a sharpened tip;
   a fluid pump providing a flow of fluid to the needle,
   a controller for controlling the fluid pump to control the flow of fluid to the needle;
   a sensor for detecting a fluid pressure in the needle; and
   a conductive element for providing an electric nerve stimulation at the tip of the needle;
   wherein the controller is disposed in communication with the conductive element, and is configured to provide through the conductive element varying electrical stimulation in response to the sensor detecting a fluid pressure above a first threshold,
   wherein the controller is configured to store a plurality of charge profiles that include data regarding various characteristics of the electrical stimulation to be provided; and
   wherein the charge profiles include a maximum charge current and a minimum charge current.

3. The system of claim 2, wherein the charge profiles include a plurality of charge current values between the maximum and the minimum.

4. The system of claim 3 wherein the controller is configured to provide a constant stimulation at a baseline current when the detected fluid pressure is below the first threshold; and wherein the charge profiles include the baseline current and the first pressure threshold.

5. A system for providing a peripheral nerve block to a patient, comprising:
   a needle having a sharpened tip;
   a fluid pump providing a flow of fluid to the needle,
   a controller for controlling the fluid pump to control the flow of fluid to the needle;
   a sensor for detecting a fluid pressure in the needle; and
   a conductive element for providing an electric nerve stimulation at the tip of the needle;
   wherein the controller is disposed in communication with the conductive element, and is configured to provide through the conductive element varying electrical stimulation in response to the sensor detecting a fluid pressure above a first threshold, and
   wherein the controller is configured to control the fluid pump to provide a dose of fluid in response to a signal from the sensor indicative of a pressure exceeding a threshold and an absence of a signal indicative of an electric motor response in response to electric nerve stimulation exceeding a threshold intensity.

6. The system of claim 1, 2, or 5 comprising a remote actuator for providing a signal to control operation of the fluid pump or the electric nerve stimulation.

7. The system of claim 1, 2, or 5 comprising an output element configured to provide a human perceptible signal in response to a determination that the tip of the needle is within a nerve.

8. The system of claim 1, 2, or 5 comprising an input element configured to allow an operator to indicate whether an evoked motor response was observed in response to the electric nerve stimulation.

9. The system of claim 1, 2, or 5 comprising a sensor for detecting an evoked motor response in response to the electric nerve stimulation.

10. The system of claim 9 wherein the sensor for detecting an evoked motor response comprises an accelerometer or electromyograph sensor.

11. The system of claim 2 or 5 wherein the controller is configured to discontinue the flow of fluid to the needle in response to the sensor detecting a fluid pressure above a second threshold and an indication of an evoked muscle response from the electric nerve stimulation.

12. The system of claim 11 wherein the second threshold is different from the first threshold.

13. The system of claim 11 wherein the second threshold is the same as the first threshold.

* * * * *